United States Patent
Audonnet et al.

(12) 
(10) Patent No.: US 6,207,166 B1
(45) Date of Patent: Mar. 27, 2001

(54) POLYNUCLEOTIDE FORMULATION AGAINST PATHOLOGIES OF THE HORSE

(75) Inventors: Jean-Christophe Audonnet; Annabelle Bouchardon, both of Lyons; Michel Riviere, Ecully, all of (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/232,478

(22) Filed: Jan. 15, 1999

Related U.S. Application Data

(63) Continuation-in-part of application No. PCT/FR97/01314, filed on Jul. 15, 1997.

(30) Foreign Application Priority Data

Jul. 19, 1996 (FR) .................................................. 96 09400

(51) Int. Cl.[7] ........................ A61K 39/12; A61K 39/295; A61K 39/145
(52) U.S. Cl. ..................................... 424/199.1; 424/202.1; 424/204.1; 424/209.1; 435/320.1; 536/23.72
(58) Field of Search ................................. 424/199.1, 820, 424/202.1, 204.1, 209.1; 435/320.1; 536/23.72

(56) References Cited

FOREIGN PATENT DOCUMENTS

| | | |
|---|---|---|
| 0304786 A2 | 3/1989 | (EP) . |
| 0447303 A1 | 9/1991 | (EP) . |
| WO 93/19183 | 9/1993 | (WO) . |
| WO 95/20660 | 8/1995 | (WO) . |

OTHER PUBLICATIONS

O'Meara et al. Immunology and Cell Biology, 1993, vol. 71 (pt 5), pp. 473–488, Oct. 1993.*
Cox et al. Journal of Virology, 1993, vol. 67 (9), pp. 5664–5667, Sep. 1993.*
Haynes et al. Journal of Biotechnology, 1996, vol. 44, pp. 37–42.*
Xiang et al. Immunity, 1995, vol. 2, pp. 129–135, Feb. 1995.*
Xiang et al. Virology, 1995, vol. 209, pp. 569–579, 1995.*
Jeffrey B. Ulmer, et al., "Heterologous Protection Against Influenza by Injection of DNA Encoding Viral Protein", Science, vol. 259 (1993) pp. 1745–1749.

* cited by examiner

*Primary Examiner*—Ali R. Salimi
(74) *Attorney, Agent, or Firm*—Frommer Lawrence & Haug LLP; William S. Frommer; Thomas J. Kowalski

(57) ABSTRACT

Disclosed and claimed is: an immunogenic or vaccine composition for inducing in an equine host an immunological response against equine rhinopneumonitis virus (EHV) containing at least one plasmid that contains and expresses in vivo in an equine host cell nucleic acid molecule(s) having sequence(s) encoding EHV gB, gD, or gB and gD; an immunogenic or vaccine composition for inducing in an equine host immunological response against encephalomyelitis virus containing at least one plasmid that contains and expresses in vivo in an equine host cell nucleic acid molecule(s) having sequence(s) encoding encephalomyelitis virus C, E2, or C and E2 proteins; and, methods for using and kits employing such compositions.

27 Claims, 21 Drawing Sheets

```
   1 ATGAAGACAACCATTATTTTGATACTACTGACCCATTGGGTCTACAGTCAAAACCCAACCAGT
   1▶ MetLysThrThrIleIleLeuIleLeuLeuThrHisTrpValTyrSerGlnAsnProThrSer

64 GGCAACAACACAGCCACACTATGTCTGGGACACCATGCAGTAGCAAATGGAACATTGGTAAAA
  22▶ GlyAsnAsnThrAlaThrLeuCysLeuGlyHisHisAlaValAlaAsnGlyThrLeuValLys

127 ACAATAACTGACGACCAAATTGAGGTGACAAATGCTACTGAATTAGTTCAGAGCACTTCAATA
  43▶ ThrIleThrAspAspGlnIleGluValThrAsnAlaThrGluLeuValGlnSerThrSerIle

190 GGGAAAATATGCAACAACCCATATAGGGTTCTAGATGGAAGAAACTGCACATTAATAGATGCA
  64▶ GlyLysIleCysAsnAsnProTyrArgValLeuAspGlyArgAsnCysThrLeuIleAspAla

253 ATGCTAGGAGATCCCCACTGTGATGTTTTTCAGTATGAGAATTGGGACCTCTTCATAGAAAGA
  85▶ MetLeuGlyAspProHisCysAspValPheGlnTyrGluAsnTrpAspLeuPheIleGluArg

316 AGCAGCGCTTTCAGCAATTGCTACCCATATGACATCCCTGACTATGCATCGCTCCGGTCTATT
 106▶ SerSerAlaPheSerAsnCysTyrProTyrAspIleProAspTyrAlaSerLeuArgSerIle

379 GTGGCATCTTCAGGAACATTAGAATTCACAGCAGAGGGATTCACATGGACAGGTGTCACTCAA
 127▶ ValAlaSerSerGlyThrLeuGluPheThrAlaGluGlyPheThrTrpThrGlyValThrGln

442 AACGGAAGAAGTGGCGCCTGCAGAAGGGGATCAGCCGATAGTTTCTTTAGCCGACTGAATTGG
 148▶ AsnGlyArgSerGlyAlaCysArgArgGlySerAlaAspSerPhePheSerArgLeuAsnTrp

505 CTAACAGAATCTGGAAATTCTTACCCCACATTGAATGTAACAATGCCTAACAATAACAATTTC
 169▶ LeuThrGluSerGlyAsnSerTyrProThrLeuAsnValThrMetProAsnAsnAsnAsnPhe

568 GATAAACTATACATCTGGGGGATCCATCACCCGAGCACAAACAATGAGCAGACAAAATTGTAT
 190▶ AspLysLeuTyrIleTrpGlyIleHisHisProSerThrAsnAsnGluGlnThrLysLeuTyr

631 GTCCAAGAATTAGGGCGAGTAACAGTCTCAACAAAAAGAAGTCAACAAACAATAATCCCCAAC
 211▶ ValGlnGluLeuGlyArgValThrValSerThrLysArgSerGlnGlnThrIleIleProAsn

694 ATCGGATCTAGACCGGGGGTCAGGGGTCAATCAGGCAGGATAAGCATATATTGGACCATTGTG
 232▶ IleGlySerArgProGlyValArgGlyGlnSerGlyArgIleSerIleTyrTrpThrIleVal

757 AAACCTGGAGATATCCTAATGATAAACAGTAATGGCAACTTAGTTGCACCGCGGGGATATTTC
 253▶ LysProGlyAspIleLeuMetIleAsnSerAsnGlyAsnLeuValAlaProArgGlyTyrPhe

820 AAAATGCGAACAGGAAAAAGCTCTATAATGAGATCAGATGCACCCATAGACACTTGTGTGTCC
 274▶ LysMetArgThrGlyLysSerSerIleMetArgSerAspAlaProIleAspThrCysValSer

883 GAGTGTATTACACCAAATGGAAGCATCCCCAACGACAAACCATTTCAAAATGTGAACAAAGTT
 295▶ GluCysIleThrProAsnGlySerIleProAsnAspLysProPheGlnAsnValAsnLysVal

946 ACATATGGAAAATGCCCCAAGTATATCAAGCAGAATACTTTGAAGCTGGCCACTGGGATGAGG
 316▶ ThrTyrGlyLysCysProLysTyrIleLysGlnAsnThrLeuLysLeuAlaThrGlyMetArg

1009 AATGTACCAGAAAAGCAAATCAGAGGAATCTTTGGAGCAATAGCGGGATTCATAGAAAATGGC
 337▶ AsnValProGluLysGlnIleArgGlyIlePheGlyAlaIleAlaGlyPheIleGluAsnGly

1072 TGGGAGGGAATGGTTGATGGGTGGTATGGATTCCGATATCAGAATTCGGAAGGAACAGGACAA
 358▶ TrpGluGlyMetValAspGlyTrpTyrGlyPheArgTyrGlnAsnSerGluGlyThrGlyGln

1135 GCTGCAGATCTAAAGAGCACTCAAGCAGCCATCGACCAGATCAATGGAAAATTGAACAGAGTG
 379▶ AlaAlaAspLeuLysSerThrGlnAlaAlaIleAspGlnIleAsnGlyLysLeuAsnArgVal
```

FIG. 8a    FIG. 8

| FIG. 8a |
|---|
| FIG. 8b |

1198 ATTGAGAGGACCAATGAGAAATTCCATCAAATAGAGAAGGAATTCTCAGAAGTAGAAGG(
400▶ IleGluArgThrAsnGluLysPheHisGlnIleGluLysGluPheSerGluValGluGl:

1261 ATCCAGGACTTGGAGAAGTATGTAGAAGACACCAAA/.TAGACCTATGGTCCTACAATGC/
421▶ IleGlnAspLeuGluLysTyrValGluAspThrLysIleAspLeuTrpSerTyrAsnAl:

1324 TTACTGGTGGCTCTAGAAAATCAACATACGATTGACTTAACAGATGCAGAGATGAATAA/
442▶ LeuLeuValAlaLeuGluAsnGlnHisThrIleAspLeuThrAspAlaGluMetAsnLys

1387 TTCGAGAAGACTAGGCGCCAGTTAAGAGAAAACGCGGAAGACATGGGGGGTGGATGTTTC
463▶ PheGluLysThrArgArgGlnLeuArgGluAsnAlaGluAspMetGlyGlyGlyCysPhe

1450 ATTTATCACAAATGTGATAATGCATGCATTGGATCAATAAGAAATGGGACATATGACCAT
484▶ IleTyrHisLysCysAspAsnAlaCysIleGlySerIleArgAsnGlyThrTyrAspHis

1513 ATATACAGAGATGAAGCATTAAACAACCGATTTCAAATTAAAGGTGTTGAGTTGAAATCA
505▶ IleTyrArgAspGluAlaLeuAsnAsnArgPheGlnIleLysGlyValGluLeuLysSer

1576 TACAAAGATTGGATACTGTGGATTTCATTCGCCATATCATGCTTCTTAATTTGCGTTGTT
526▶ TyrLysAspTrpIleLeuTrpIleSerPheAlaIleSerCysPheLeuIleCysValVal

1639 TTGGGTTTCATTATGTGGGCTTGCCAAAAAGGCAACATCAGATGCAACATTTGCATTTGA
547▶ LeuGlyPheIleMetTrpAlaCysGlnLysGlyAsnIleArgCysAsnIleCysIle•••

SEQUENCE LISTING

<160> NUMBER OF SEQ ID NOS: 36

<210> SEQ ID NO 1
<211> LENGTH: 32
<212> TYPE: DNA
<213> ORGANISM: Borrelia burgdorferi

<400> SEQUENCE: 1
aaaactgcag ccgtcatgtc ctctggttgc cg                                32

<210> SEQ ID NO 2
<211> LENGTH: 39
<212> TYPE: DNA
<213> ORGANISM: Borrelia burgdorferi

<400> SEQUENCE: 2
ataagaagcg gccgctaaac atgtttaaac cattttttc                         39

<210> SEQ ID NO 3
<211> LENGTH: 38
<212> TYPE: DNA
<213> ORGANISM: Borrelia burgdorferi

<400> SEQUENCE: 3
aaaactgcag acatgtccac ttgttgccgt gctatttg                          38

<210> SEQ ID NO 4
<211> LENGTH: 36
<212> TYPE: DNA
<213> ORGANISM: Borrelia burgdorferi

<400> SEQUENCE: 4
ctagtctaga ttaaaccatt ttttcgcttt ccatgg                            36

<210> SEQ ID NO 5
<211> LENGTH: 32
<212> TYPE: DNA
<213> ORGANISM: Borrelia burgdorferi

<400> SEQUENCE: 5
aaaactgcag catgtctacc ttcaagctta tg                                32

<210> SEQ ID NO 6
<211> LENGTH: 37
<212> TYPE: DNA
<213> ORGANISM: Borrelia burgdorferi

<400> SEQUENCE: 6
cgcggatcct tacggaagct gggtatattt aacatcc                           37

<210> SEQ ID NO 7
<211> LENGTH: 33
<212> TYPE: DNA
<213> ORGANISM: Borrelia burgdorferi

<400> SEQUENCE: 7
aaaactgcag atatgtctac cttcaagcct atg                               33

<210> SEQ ID NO 8
<211> LENGTH: 33
<212> TYPE: DNA
<213> ORGANISM: Borrelia burgdorferi -continued

<400> SEQUENCE: 8
cgcggatcct tacggaagct gagtatattt gac                          33

<210> SEQ ID NO 9
<211> LENGTH: 36
<212> TYPE: DNA
<213> ORGANISM: Borrelia burgdorferi

<400> SEQUENCE: 9
acgcgtcgac atgaacactc aaattctaat attagc                       36

<210> SEQ ID NO 10
<211> LENGTH: 35
<212> TYPE: DNA
<213> ORGANISM: Borrelia burgdorferi

<400> SEQUENCE: 10
cgcggatccc ttatatacaa atagtgcacc gcatg                        35

<210> SEQ ID NO 11
<211> LENGTH: 33
<212> TYPE: DNA
<213> ORGANISM: Borrelia burgdorferi

<400> SEQUENCE: 11
acgcgtcgac gcatgaagac aaccattatt ttg                          33

<210> SEQ ID NO 12
<211> LENGTH: 34
<212> TYPE: DNA
<213> ORGANISM: Borrelia burgdorferi

<400> SEQUENCE: 12
cgcggatcct caaatgcaaa tgttgcatct gatg                         34

<210> SEQ ID NO 13
<211> LENGTH: 32
<212> TYPE: DNA
<213> ORGANISM: Borrelia burgdorferi

<400> SEQUENCE: 13
tttgcggccg catgaagaca accattattt tg                           32

<210> SEQ ID NO 14
<211> LENGTH: 35
<212> TYPE: DNA
<213> ORGANISM: Borrelia burgdorferi

<400> SEQUENCE: 14
tttgcggccg cttactcaaa tgcaaatgtt gcatc                        35

<210> SEQ ID NO 15
<211> LENGTH: 1698
<212> TYPE: DNA
<213> ORGANISM: Borrelia burgdorferi

<400> SEQUENCE: 15
atgaagacaa ccattatttt gatactactg acccattggg tctacagtca aaacccaacc     60
agtggcaaca acacagccac actatgtctg ggacaccatg cagtagcaaa tggaacattg    120
gtaaaaacaa taactgacga ccaaattgag gtgacaaatg ctactgaatt agttcagagc    180

-continued

| | |
|---|---|
| acttcaatag ggaaaatatg caacaaccca tataggttc tagatggaag aaactgcaca | 240 |
| ttaatagatg caatgctagg agatccccac tgtgatgttt ttcagtatga aattgggac | 300 |
| ctcttcatag aaagaagcag cgctttcagc aattgctacc catatgacat ccctgactat | 360 |
| gcatcgctcc ggtctattgt ggcatcttca ggaacattag aattcacagc agagggattc | 420 |
| acatggacag tgtcactca aaacggaaga agtggcgcct gcagaagggg atcagccgat | 480 |
| agtttcttta gccgactgaa ttggctaaca gaatctggaa attcttaccc cacattgaat | 540 |
| gtaacaatgc ctaacaataa caatttcgat aaactataca tctgggggat ccatcacccg | 600 |
| agcacaaaca atgagcagac aaaattgtat gtccaagaat tagggcgagt aacagtctca | 660 |
| acaaaaagaa gtcaacaaac aataatcccc aacatcggat ctagaccggg ggtcaggggt | 720 |
| caatcaggca ggataagcat atattggacc attgtgaaac ctggagatat cctaatgata | 780 |
| aacagtaatg caacttagt tgcaccgcgg ggatatttca aaatgcgaac aggaaaaagc | 840 |
| tctataatga gatcagatgc acccatagac acttgtgtgt ccgagtgtat tacaccaaat | 900 |
| ggaagcatcc ccaacgacaa accatttcaa aatgtgaaca agttacata tggaaaatgc | 960 |
| cccaagtata tcaagcagaa tactttgaag ctggccactg ggatgaggaa tgtaccagaa | 1020 |
| aagcaaatca gaggaatctt tggagcaata gcgggattca tagaaaatgg ctggagggga | 1080 |
| atggttgatg gtggtatgg attccgatat cagaattcgg aaggaacagg acaagctgca | 1140 |
| gatctaaaga gcactcaagc agccatcgac cagatcaatg gaaaattgaa cagagtgatt | 1200 |
| gagaggacca atgagaaatt ccatcaaata gagaggaat tctcagaagt agaagggaga | 1260 |
| atccaggact ggagaagta tgtagaagac accaaaatag acctatggtc ctacaatgca | 1320 |
| gagttactgg tggctctaga aaatcaacat acgattgact taacagatgc agagatgaat | 1380 |
| aaattattcg agaagactag gcgccagtta agagaaaacg cggaagacat gggggtgga | 1440 |
| tgtttcaaga tttatcacaa atgtgataat gcatgcattg gatcaataag aaatgggaca | 1500 |
| tatgaccatt acatatacag agatgaagca ttaaacaacc gatttcaaat taaaggtgtt | 1560 |
| gagttgaaat caggctacaa agattggata ctgtggattt cattcgccat atcatgcttc | 1620 |
| ttaatttgcg ttgttctatt gggtttcatt atgtgggctt gccaaaaagg caacatcaga | 1680 |
| tgcaacattt gcatttga | 1698 |

<210> SEQ ID NO 16
<211> LENGTH: 32
<212> TYPE: DNA
<213> ORGANISM: Borrelia burgdorferi

<400> SEQUENCE: 16

| | |
|---|---|
| ccggtcgaca tggcgtctca aggcaccaaa cg | 32 |

<210> SEQ ID NO 17
<211> LENGTH: 34
<212> TYPE: DNA
<213> ORGANISM: Borrelia burgdorferi

<400> SEQUENCE: 17

| | |
|---|---|
| cgcggatcct taattgtcaa actcttctgc attg | 34 |

<210> SEQ ID NO 18
<211> LENGTH: 34
<212> TYPE: DNA
<213> ORGANISM: Borrelia burgdorferi

<400> SEQUENCE: 18

-continued cgcggatcct taattgtcat attcctctgc attg					34

<210> SEQ ID NO 19
<211> LENGTH: 34
<212> TYPE: DNA
<213> ORGANISM: Borrelia burgdorferi

<400> SEQUENCE: 19
aaactgcaga tgaaaaatct ggattgttgg gttg					34

<210> SEQ ID NO 20
<211> LENGTH: 30
<212> TYPE: DNA
<213> ORGANISM: Borrelia burgdorferi

<400> SEQUENCE: 20
tttggatcct taatcatttg tccatccttc					30

<210> SEQ ID NO 21
<211> LENGTH: 37
<212> TYPE: DNA
<213> ORGANISM: Borrelia burgdorferi

<400> SEQUENCE: 21
acgcgtcgac tatgaaaaaa tatttattgg gaatagg					37

<210> SEQ ID NO 22
<211> LENGTH: 34
<212> TYPE: DNA
<213> ORGANISM: Borrelia burgdorferi

<400> SEQUENCE: 22
cgcggatccc ttattttaaa gcgtttttaa tttc					34

<210> SEQ ID NO 23
<211> LENGTH: 34
<212> TYPE: DNA
<213> ORGANISM: Borrelia burgdorferi

<400> SEQUENCE: 23
aaactgcaga tggatttgga cactcatttc accc					34

<210> SEQ ID NO 24
<211> LENGTH: 44
<212> TYPE: DNA
<213> ORGANISM: Borrelia burgdorferi

<400> SEQUENCE: 24
cgcggatcct caataaaaat catgccctcg tcggcttaat gcag					44

<210> SEQ ID NO 25
<211> LENGTH: 33
<212> TYPE: DNA
<213> ORGANISM: Borrelia burgdorferi

<400> SEQUENCE: 25
aaactgcaga tgttcccata ccctacactt aac					33

<210> SEQ ID NO 26
<211> LENGTH: 45
<212> TYPE: DNA
<213> ORGANISM: Borrelia burgdorferi

<400> SEQUENCE: 26
tgaagatctt caataaaaat caccatggct ctgacccctc tggtg     45

<210> SEQ ID NO 27
<211> LENGTH: 35
<212> TYPE: DNA
<213> ORGANISM: Borrelia burgdorferi

<400> SEQUENCE: 27
acgcgtcgac atgagcatta ccgatgactt cacac     35

<210> SEQ ID NO 28
<211> LENGTH: 44
<212> TYPE: DNA
<213> ORGANISM: Borrelia burgdorferi

<400> SEQUENCE: 28
cgcggatcct caataaaaat caagcgttgg ttggccgaat acag     44

<210> SEQ ID NO 29
<211> LENGTH: 34
<212> TYPE: DNA
<213> ORGANISM: Borrelia burgdorferi

<400> SEQUENCE: 29
acgcgtcgac atgtttccat accctcagct gaac     34

<210> SEQ ID NO 30
<211> LENGTH: 44
<212> TYPE: DNA
<213> ORGANISM: Borrelia burgdorferi

<400> SEQUENCE: 30
cgcggatcct caataaaaat caccacggtt cagaaccttc gggg     44

<210> SEQ ID NO 31
<211> LENGTH: 35
<212> TYPE: DNA
<213> ORGANISM: Borrelia burgdorferi

<400> SEQUENCE: 31
acgcgtcgac atgtccaccg aggagctgtt taagg     35

<210> SEQ ID NO 32
<211> LENGTH: 44
<212> TYPE: DNA
<213> ORGANISM: Borrelia burgdorferi

<400> SEQUENCE: 32
cgcggatcct caataaaaat caggcccggg cagtgcgggc gcag     44

<210> SEQ ID NO 33
<211> LENGTH: 30
<212> TYPE: DNA
<213> ORGANISM: Borrelia burgdorferi

<400> SEQUENCE: 33
aaactgcaga tgttcccgtt ccagccaatg     30

<210> SEQ ID NO 34
<211> LENGTH: 45
<212> TYPE: DNA
<213> ORGANISM: Borrelia burgdorferi

```
<400> SEQUENCE: 34
cgcggatcct caataaaaat caccattgct cgcagttctc cggag            45

<210> SEQ ID NO 35
<211> LENGTH: 33
<212> TYPE: DNA
<213> ORGANISM: Borrelia burgdorferi

<400> SEQUENCE: 35
aaaactgcag agatggttcc tcaggctctc ctg                         33

<210> SEQ ID NO 36
<211> LENGTH: 34
<212> TYPE: DNA
<213> ORGANISM: Borrelia burgdorferi

<400> SEQUENCE: 36
cgcggatcct cacagtctgg tctcaccccc actc                        34
```

POLYNUCLEOTIDE FORMULATION AGAINST PATHOLOGIES OF THE HORSE

This is a continuation-in-part of copending International Application PCT/FR97/01314 having an international filing date of Jul. 15, 1997, and designating the U.S. and claiming priority from French Application No. 96/09400, filed Jul. 19, 1996. Reference is also made to the concurrently filed applications of Audonnet et al., Ser. Nos. 09/232,278, 09/232,468, 09/232,477, 09/232,279 and 09/232,479 and to the concurrently filed application of Rijsewijk et al. Ser. No. 09/232,469. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors(e.g., one or more or all of regulatory sequences such as DNA for promoter, leader for secretion, terminator), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formulation for vaccinating equidae, in particular horses. It also relates to a corresponding vaccination method.

A relatively wide variety of horse pathologies exist. Apart from the well-known respiratory pathologies, such as rhinopneumonitis and influenza, horses are susceptible, in particular on the American continent, to various encephalomyelites. Finally, horses exhibit a variety of other pathologies among which tetanus, Lyme disease and equine arteritis may be mentioned, in particular, without forgetting the risks of exposure to the rabies virus.

The circumstances under which horses are exposed to various pathogenic microorganisms have been increased by the movement of large numbers of horses over substantial distances by land or by air, such that the risk of infection tends to increase.

However, in view of the high cost of these animals, in particular in the case of breeding animals, important to control, as far as possible, the risks of unavailable for long periods, if not actually being lost. A certain number of horse vaccines, whose efficacy varies, already exist.

Thus, inactivated or subunit vaccines, all of which, however exhibit some limitations expressed as incomplete or short-term protection and, possibly, safety problems linked to the adjuvants employed, have been developed for the equine rhinopneumonitis which is caused by the different strains of equine herpesvirus (EHV).

Attempts are also being made to use vaccination to prevent equine influenza, which is another important pathology. The vaccines employed are inactivated or subunit vaccines which, while they are effective to a certain degree, are nevertheless not without problems. Thus, protection is frequently not complete and is generally of a relatively brief duration, thereby requiring revaccinations, as in the case of rhinopneumonitis. Safety problems may also be encountered.

Vaccines based on antitetanus toxoid have also been developed and are undeniably effective.

Vaccines against encephalomyelites, some eastern encephalomyelites, western encephalomyelitis and Venezuelan encephalomyelitis, whose efficacy is still poorly known, also exist.

For reasons of economy, on the one hand, and the rational management of equine vaccinations on the other, multivalent vaccine formulations have already been proposed for preventing several of these infectious diseases.

The combinations which have so far been developed have been achieved using inactivated vaccines or live vaccines and, where appropriate, mixtures of these compatibility between valencies and of stability. Thus, it is necessary to ensure compatibility between the different valencies, both with regard to the different antigens employed and with regard to the formulations themselves, in particular when inactivated vaccines and live vaccines are combined at the same time. There is also the problem of preserving such combined vaccines and also that of their safety, in particular in the presence of adjuvant. In general, these vaccines are relatively expensive.

Furthermore, these formulations have not enabled three of the main valencies, namely the equine influenza, rhinopneumonitis, in particular EHV-1 and EHV-4, and tetanus valencies, to be combined. For example, combinations of the influenza and encephalomyelitis valencies, or of the rhinopneumonitis and encephalomyelitis valencies, are known.

The Patent Applications WO-A-90 11 092, WO-A-93 19 183, WO-A-94 21 797 and WO-A-95 20 660 have proposed using the recently developed technique of polynucleotide vaccines. It is known that these vaccines use a plasmid which is capable of expressing, in the host cells, the antigen which is inserted into the plasmid. All the routes of administration have been proposed (intraperitoneal, intravenous, intramuscular, transcutaneous, intradermal, mucosal, etc.). Different means of vaccination may also be used, such as DNA deposited on the surface of gold particles and projected so as to penetrate into the skin of the animal (Tang et al., Nature 356, 152–154, 1992) and injections by means of a liquid jet, which makes it possible to transfect, at one and the same time, skin, muscle, fatty tissues and mammary tissues (Furth et al., Analytical Biochemistry, 205, 365–368, 1992). (See also U.S. Pat. Nos. 5,846,946, 5,620,896, 5,643, 578, 5,580,589, 5,589,466, 5,693,622, and 5,703,055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.)

The polynucleotide vaccines can use both naked DNAs and formulated DNAs, for example within liposomes or cationic lipids.

Polynucleotide vectors which integrate the HA or NT genes have been tried out in mice, ferrets and chickens in the case of the influenza virus. No data are available for the horse.

With regard to tetanus, it has recently been reported that immunization of mice with a plasmid which expresses the non-toxic C-terminal region of the tetanus toxin, together with the C fragment, induced the appearance of seroprotective antibodies in the mouse.

However, it is not possible to transpose directly the teaching of the results obtained in these animals of short lifespan to other mammals, in particular mammals of large size.

There is still a requirement, therefore, to improve the protection of equidae, in particular horses, against infectious pathologies.

The invention proposes to provide a multivalent vaccine formulation which makes it possible to vaccinate equidae, in particular horses, against a number of pathogenic agents.

Another object of the invention is to provide such a vaccine formulation which combines different valencies while at the same time exhibiting the requisite criteria of compatibility and stability of the valencies between themselves.

Another object of the invention is to provide such a vaccine formulation which makes it possible to combine different valencies in one and the same excipient.

Another object of the invention is to provide such a vaccine formulation which is easy to implement and inexpensive.

Yet another object of the invention is to provide such a formulation and a method of vaccinating horses which makes it possible to obtain a protection, including a multivalent protection, which is associated with a high level of efficacy and is of long duration while exhibiting a high degree of safety.

The present invention therefore relates to a vaccine formulation against pathologies of equidae, in particular horses, which comprises at least 3 polynucleotide vaccine valencies, each of which comprises a plasmid integrating so as to express it, in vivo in the cells, a gene of an equine pathogen valency, with these valencies being selected from the group consisting of equine rhinopneumonitis virus, EHV, equine influenza virus, EIV, and tetanus (Cl. tetani), with these plasmids comprising, for each valency, one or more of the genes selected from the group consisting of gB and gD in the case of the equine rhinopneumonitis virus, HA, NP and N in the case of the equine influenza virus, and a gene which encodes all or part of the C subunit of the tetanus toxin.

In the present invention, valency is understood as meaning at least one antigen which ensures protection against the virus of the pathogen under consideration, with the valency being able to contain, as a subvalency, one or more natural or modified genes of one or more strains of the pathogen under consideration.

Pathogenic agent gene is understood as meaning not only the complete gene but also the different nucleotide sequences, including fragments, which retain the ability to induce a protective response. The gene concept covers the nucleotide sequences which are equivalent to those described precisely in the examples, that is to say the sequences which are different but which encode the same protein. It also covers the nucleotide sequences of other strains of the pathogen under consideration which ensure crossprotection or a protection which is specific for a strain or a group of strains. It also covers the nucleotide sequences which have been modified in order to facilitate expression in vivo by the animal host but which encode the same protein.

Thus, particularly preferably, the vaccine according to the invention comprises, in the equine rhinopneumonitis valency, at least one antigen from the EHV-1 strain and at least one antigen from the EHV-4 strain, with these antigens preferably being the same type of antigen.

The therapeutically effective quantities of the polynucleotide valencies are contained, or are intended to be contained, in an excipient which is suitable for administering to the animal, preferably for intramuscular administration. Preferably, this excipient is an aqueous excipient which lacks oily constituents.

With regard to the equine rhinopneumonitis valency, preference is given to combining the gB and gD genes, preferably from EHV strains, in particular the 1 and 4 strains.

With regard to the equine influenza valency, preference is given to using the gene which encodes the haemagglutinin HA or to using the combination of the genes which encode HA and NP. The influenza virus HA sequences, in particular from the different strains encountered in the territory, are preferably combined in one and the same vaccine. On the other hand, NP ensures crossprotection and it is possible, therefore, to be contented with the sequence from one single strain of the virus.

In the case of the tetanus valency, preference is given to the C subunit, where appropriate modified by mutation or deletion.

Combining genes which encode several antigens of one and the same valency or of one and the same strain in a valency can be effected by mixing plasmids which express a single antigen or, on the contrary, by inserting several genes into one and the same plasmid.

While combining the different valencies of the vaccine according to the invention can preferably be effected by mixing polynucleotide plasmids which express one or more antigens of each valency, it is also possible to envisage having several antigens of several valencies being expressed by one and the same vector of the plasmid type.

In an improved form of the invention, the formulation can also include one or more other valencies of other equine pathogens, in particular valencies of the eastern encephalomyelitis virus, EEV, of the western encephalomyelitis virus, WEV, and of the Venezuelan encephalomyelitis virus, VEV, preferably all three simultaneously.

These valencies can also advantageously include the valency of Lyme disease, *B. burgdorferi,* of equine arteritis (EAV) and of rabies.

The genes of the abovementioned encephalomyelites which are used are the genes for the C and E2 antigens, preferably the E2 gene on its own or the combination of the two genes E2 and C.

In the case of the Lyme disease valency, a selection is made between the OspA, OspB and p100 genes, with OspA being preferred.

In the case of equine arteritis, the E, M and N genes, which are used either on their own or in combination are selected.

In the case of rabies, the G gene is selected.

A vaccine formulation according to the invention can be presented in a dose volume of between 0.1 and 10 ml, in particular of between 1 and 5 ml.

The dose is generally between 10 ng and 1 mg, in particular between 100 ng and 500 $\mu$g, preferably between 1 $\mu$g and 250 $\mu$g per plasmid type.

Preference is given to using naked plasmids, which are simply placed in the vaccination excipient, which is in general physiological saline (0.9% NaCl) , ultrapure water, TE buffer, etc. It is, of course, possible to use all the polynucleotide vaccine formulations described in the prior art.

Each plasmid comprises a promoter which is capable of ensuring expression of the inserted gene under its control in the host cells. In general, the promoter is a strong eukaryotic promoter, in particular an early promoter of the cytomegalovirus CMV-IE of human or murine origin, or else, where appropriate, of another origin such as rat, pig or guinea pig.

More generally, the promoter can be either of viral origin or of cellular origin. Viral promoters other than the CMV-IE promoter which may be mentioned are the early or later promoters of the SV 40 virus or the LTR promoter of the Rous sarcoma virus. The promoter can also be a promoter of the virus from which the gene is derived, for example the gene's own promoter.

A cellular promoter which may be mentioned is the promoter of a gene of the cytoskeleton, for example the desmin promoter (Polmont et al., Journal of Submicroscopic Cytology and Pathology, 1990, 22, 117–122; and Zhenlin et al., Gene, 1989, 78, 243–254), or else the actin promoter.

When several genes are present in one and the same plasmid, they may be presented within the same transcription unit or within two different units.

The invention also relates to monovalent vaccine formulations which comprise one or more plasmids which encode one or more genes of one of the abovementioned pathogenic agents, in particular of rhinopneumonitis or of Lyme disease, of equine arteritis, of equine encephalomyelitis, of western encephalomyelitis and of Venezuelan encephalomyelitis, with the genes being those described above. These formulations can comprise the above-mentioned features as regards the choice of the genes from one and the same pathogen and their combination, the composition of the plasmids, the dose volumes, the dosages, etc.

The present invention also relates to a method of vaccinating equidae, in particular horses, against infectious diseases, which method comprises administering an effective dose of a multivalent or monovalent vaccine formulation such as described above.

This method of vaccination comprises administering one or more doses of the vaccine formulation.

The vaccine formulations according to the invention can be administered by the different routes of administration which have been proposed within the general context of polynucleotide vaccination and using known administration techniques. However, the intramuscular route is distinctly preferred.

It is also possible to vaccinate by the intradermal route by means of a liquid jet, preferably by means of multiple jets, with the aid of an injector, in particular an injector which uses an injection head which is fitted with several holes or nozzles, in particular, from 5 to 6 holes or nozzles, such as the Pigjet appliance, which is produced and distributed by the firm Endoscoptic, Laons, France.

The dose volume in the case of such an appliance is preferably reduced to between 0.1 and 0.9 ml, in particular between 0.2 and 0.6 ml, and advantageously between 0.4 and 0.5 ml, with it being possible for the volume to be administered in one or more, preferably 2, applications.

The abovementioned monovalent vaccines can be used, in particular, for preparing the polyvalent vaccine according to the invention.

The monovalent vaccine formulations can also be used in combination with a vaccine of another type (whole live or inactivated, recombinant or subunit) against another pathology or as a booster for a vaccine as described below.

Thus, the present invention also relates to the use of one or more plasmids according to the invention for producing a vaccine which is intended for vaccinating horses which have been initially vaccinated with a conventional first vaccine (monovalent or multivalent) which is of the same type as those of the prior art and which is selected, in particular, from the group consisting of whole live vaccine, whole inactivated vaccine, subunit vaccine or recombinant vaccine, with this first vaccine exhibiting (that is to say containing or being able to express) the antigen or the antigens encoded by the plasmid or the plasmids or (an) antigen(s) which ensure(s) crossprotection.

Remarkably, the polynucleotide vaccine has a powerful booster effect which translates into an amplification of the immune response and the establishment of long-term immunity.

In general, the first-vaccination vaccines can be selected from the commercial vaccines which can be obtained from the different veterinary vaccine producers.

In one preferred embodiment of the process according to the invention, an effective dose of the conventional vaccine, in particular an inactivated, live, attenuated or recombinant vaccine, or else a subunit vaccine, is firstly administered to the animal so as to ensure an initial vaccination and the polyvalent or monovalent vaccine according to the invention is administered after a waiting period of preferably from 2 to 4 weeks.

The invention also relates to a vaccination kit which combines a vaccine formulation according to the invention and a first-vaccination vaccine such as described above. It also relates to a vaccine formulation according to the invention which is accompanied by a leaflet which indicates the use of this formulation as a booster for a first vaccination such as described above.

The invention also relates to the method for preparing the vaccination formulations, namely the preparation of the valencies and their mixtures, as is evident from this description.

The invention will now be described in more detail with the aid of embodiments of the invention which are dealt with while referring to the drawings.

BRIEF DESCRIPTION OF THE DRAWINGS

FIG. 8: Sequence of the HA Gene of the *Fontainbleau equine* influenza strain

LIST OF SEQ ID NO. SEQUENCES

SEQ ID No. 1: Oligonucleotide AB013
SEQ ID No. 2: Oligonucleotide AB014
SEQ ID No. 3: Oligonucleotide AB071
SEQ ID No. 4: Oligonucleotide AB074
SEQ ID No. 5: Oligonucleotide AB030
SEQ ID No. 6: Oligonucleotide AB031

SEQ ID No. 7: Oligonucleotide AB075
SEQ ID No. 8: Oligonucleotide AB076
SEQ ID No. 9: Oligonucleotide AB015
SEQ ID No. 10: Oligonucleotide AB016
SEQ ID No. 11: Oligonucleotide AB077
SEQ ID No. 12: Oligonucleotide AB078
SEQ ID No. 13: Oligonucleotide AB186
SEQ ID No. 14: Oligonucleotide AB187
SEQ ID No. 15: Sequence of the HA gene of the *Fontainebleau equine* influenza strain SEQ ID No. 16: Oligonucleotide AD156

SEQ ID No. 17: Oligonucleotide AB159

SEQ ID No. 18: Oligonucleotide AB157

SEQ ID No. 19: Oligonucleotide AB128

SEQ ID No. 20: Oligonucleotide AB129

SEQ ID No. 21: Oligonucleotide AB038

SEQ ID No. 22: Oligonucleotide AB039

SEQ ID No. 23: Oligonucleotide AB176

SEQ ID No. 24: Oligonucleotide AB177

SEQ ID No. 25: Oligonucleotide AB174

SEQ ID No. 26: Oligonucleotide AB175

SEQ ID No. 27: Oligonucleotide AB180

SEQ ID No. 28: Oligonucleotide AB181

SEQ ID No. 29: Oligonucleotide AB178

SEQ ID No. 30: Oligonucleotide AB179

SEQ ID No. 31: Oligonucleotide AB184

SEQ ID No. 32: Oligonucleotide AB185

SEQ ID No. 33: Oligonucleotide AB182

SEQ ID No. 34: Oligonucleotide AB183

SEQ ID No. 35: Oligonucleotide AB011

SEQ ID No. 36: Oligonucleotide AB012

EXAMPLES

Example 1

Culturing the Viruses

The viruses are cultured on the appropriate cell system until a cytopathic effect is obtained. The cell systems to be used for each virus are well known to the skilled person. Briefly, cells which are susceptible to the virus employed, and which are cultured in Eagle's minimum essential medium ("MEM" medium) or another appropriate medium, are inoculated with the viral strain under study using a multiplicity of infection of 1. The infected cells are then incubated at 37° C. for the time which is required for a complete cytopathic effect to appear (on average 36 hours).

Example 2

Culturing the Bacteria

Tetanus . . . The bacteria are cultured in the appropriate media, and under the conditions which are well known to the skilled person, so as to obtain a bacterial biomass which is sufficient for extracting the genetic material. This extraction is carried out using the customary techniques described by Sambrook J. et al. *(Molecular Cloning: A Laboratory Manual.* 2nd Edition. Cold Spring Harbor Laboratory. Cold Spring Harbor. N.Y. 1989).

The strains of *Borrelia burgdorferi* are cultured in the appropriate media and under the conditions which are well known to the skilled person. These conditions and media are described, in particular, by A. Barbour (J. Biol. Med. 1984. 57. 71–75). The bacterial DNA was extracted under the conditions described by W. Simpson et al. (Infect. Immun. 1990. 58. 847–853). The customary techniques described by J. Sambrook et al. (*Molecular Cloning: A Laborarory Manual.* 2nd Edition. Cold Spring Harbor Laboratory. Cold Spring Harbor. N.Y. 1989) can also be employed.

Example 3

Extracting the Viral Genomic DNAs

After culture, the supernatant and the lysed cells are harvested and the whole viral suspension is centrifuged at 1000 g and +4° C. for 10 minutes in order to remove the cell debris. The viral particles are then harvested by ultracentrifugation at 400,000 g and +4° C. for 1 hour. The pellet is taken up in a minimal volume of buffer (10 mM tris, 1 mM EDTA). This concentrated viral suspension is treated with proteinase K (final concentration, 100 $\mu$g/ml) in the presence of sodium dodecyl sulphate (SDS) (final concentration, 0.5%) at 37° C. for 2 hours. The viral DNA is then extracted with a phenol/chloroform mixture and then precipitated with 2 volumes of absolute ethanol. After having been stored at −20° C. overnight, the DNA is centrifuged at 10,000 g and +40° C. for 15 minutes. The DNA pellet is dried and then taken up in a minimal volume of sterile ultrapure water. It can then be digested with restriction enzymes.

Example 4

Isolating the Viral Genomic RNAs

The RNA viruses were purified using the techniques which are well known to the skilled person. The viral genomic RNA from each virus was then isolated using the "guanidium thiocyanate/phenol-chloroform" extraction technique described by P. Chomczynski and N. Sacchi (Anal. Biochem. 1987. 162. 156–159)

Example 5

Molecular Biological Techniques

All the plasmid constructions were carried out using the standard techniques of molecular biology as described by J. Sambrook et al. (*Molecular Cloning: A Laboratory Manual.* 2nd Edition. Cold Spring Harbor Laboratory. Cold Spring Harbor. N.Y. 1989). All the restriction fragments employed for the present invention were isolated using the "Geneclean" kit (BIO 101 Inc. La Jolla, Calif.).

Example 6

RT-PCR Technique

Specific oligonucleotides (which included restriction sites at their 5' ends for facilitating cloning of the amplified fragments) were synthesized such that they entirely cover the coding regions of the genes to be amplified (see specific examples). The reverse transcription (RT) reaction and the amplification by polymerase chain reaction (PCR) were carried out using the standard techniques (Sambrook J. et al. 1989). Each RT-PCR reaction was carried out using a pair of specific amplimers and taking the extracted viral genomic RNA as the template. The complementary DNA which was amplified was extracted with phenol/chloroform/isoamyl alcohol (25:24:1) before being digested with the restriction enzymes.

Example 7

Plasmid pVR1012

Figure 1:
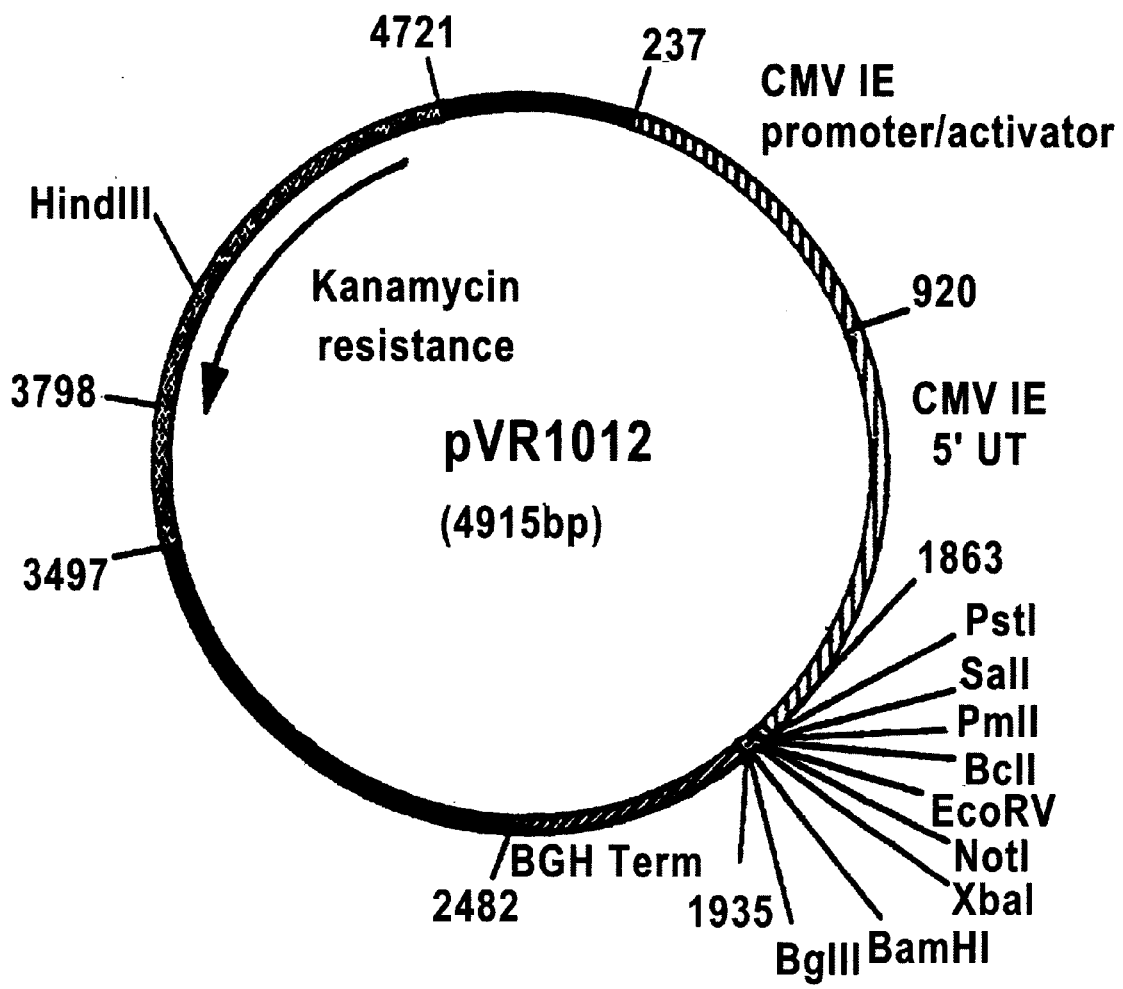
FIG. 1: Plasmid pVR1012

Plasmid pVR1012 (FIG. 1) was obtained from Vical Inc. San Diego, Calif. U.S.A. Its construction was described in J. Hartikka et al. (Human Gene Therapy, 1996. 7. 1205–1217).

Example 8

Constructing the Plasmid pAB042 (ERV-1 gB Gene)

A PCR reaction was carried out using the genomic DNA of type 1 equine herpesvirus (EHV-1) (Kentucky D strain) (P. Guo et al. J. Virol, 1990. 64. 2399–2406) and using the following oligonucleotides:

AB013 (32 mer) (SEQ ID No. 1)

5'AAAACTGCAGCCGTCATGTCCTCTGGTTGCCG 3'

AB014 (39 mer) (SEQ ID No. 2)

Figure 2:
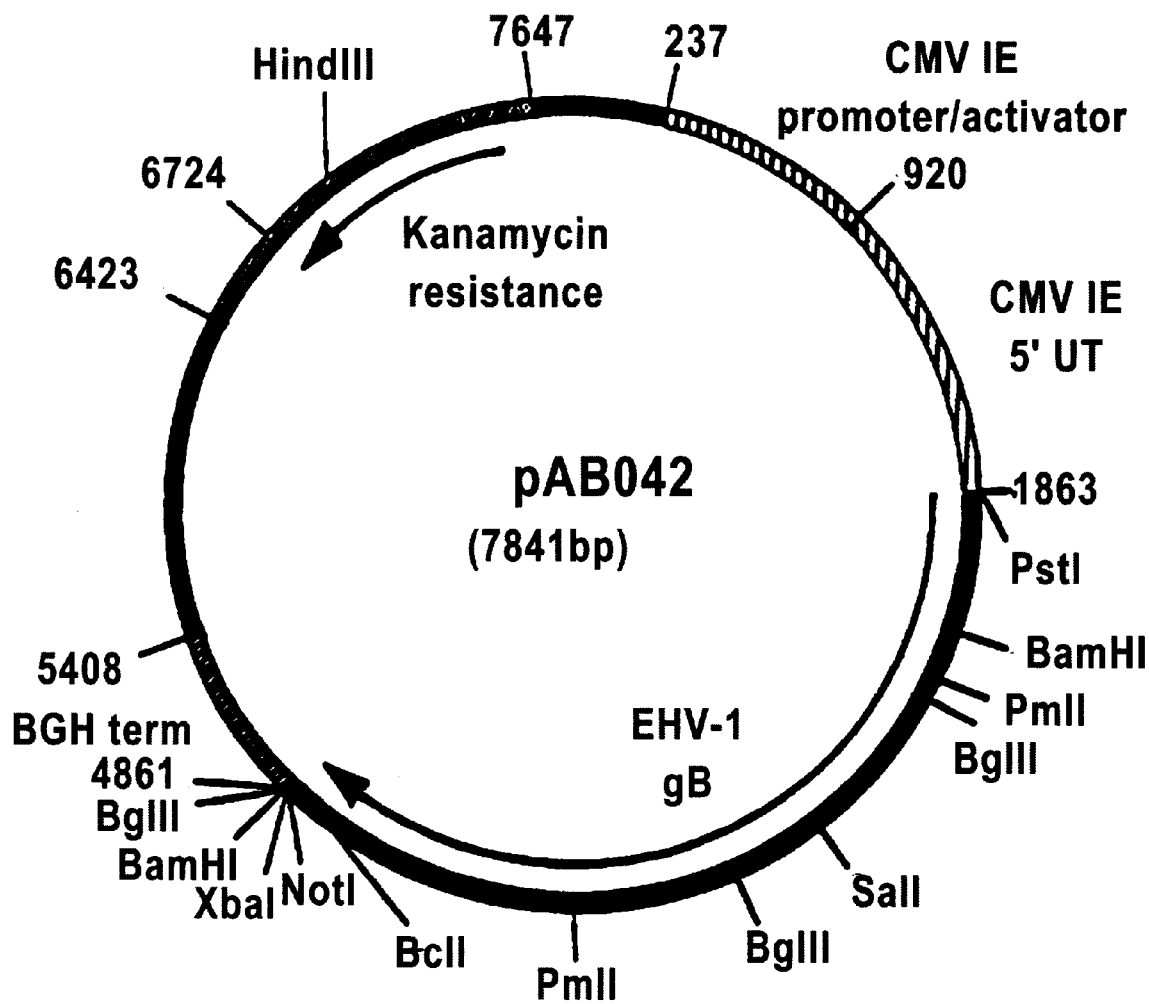
FIG. 2: Plasmid pAB042

5'ATAAGAAGCGGCCGCTAAACATGTT-TAAACCATTTTTTC 3' in order to isolate the gene encoding the gB glycoprotein (EHV-1 gB) in the form of a PstI/NotI fragment. After purification, the 2981 bp PCR product was digested with PstI and NotI in order to isolate a PstI/NotI fragment of 2959 bp in size. This fragment was ligated to the vector pVR1012 (Example 7), which had previously been digested with PstI and NotI, in order to yield the plasmid pAB042 (7841 bp) (FIG. 2).

Example 9

Constructing the Plasmid pAB031 (EHV-4 gB Gene)

A PCR reaction was carried out using the genomic DNA of type 4 equine herpesvirus (EHV-4) (strain 1942) (M. Riggio et al. J. Virol, 1989. 63. 1123–1133) and using the following oligonucleotides:

AB071 (38 mer) (SEQ ID No 3)

5'AAAACTGCAGACATGTCCACTTGTTGC-CGTGCTATTTG 3'

AB074 (36 MER) (SEQ ID No. 4)

5CTAGTCTAGATTAAAC-CATTTTTTCGCTTTCCATGG 3' in order to amplify a 2949 bp fragment which contains the gene encoding the gB glycoprotein of EHV-4 in the form of a PstI/XbaI fragment. After purification, the PCR product was digested with PstI and XbaI to give a PstI/XbaI fragment of 2931 bp in size.

Figure 3:
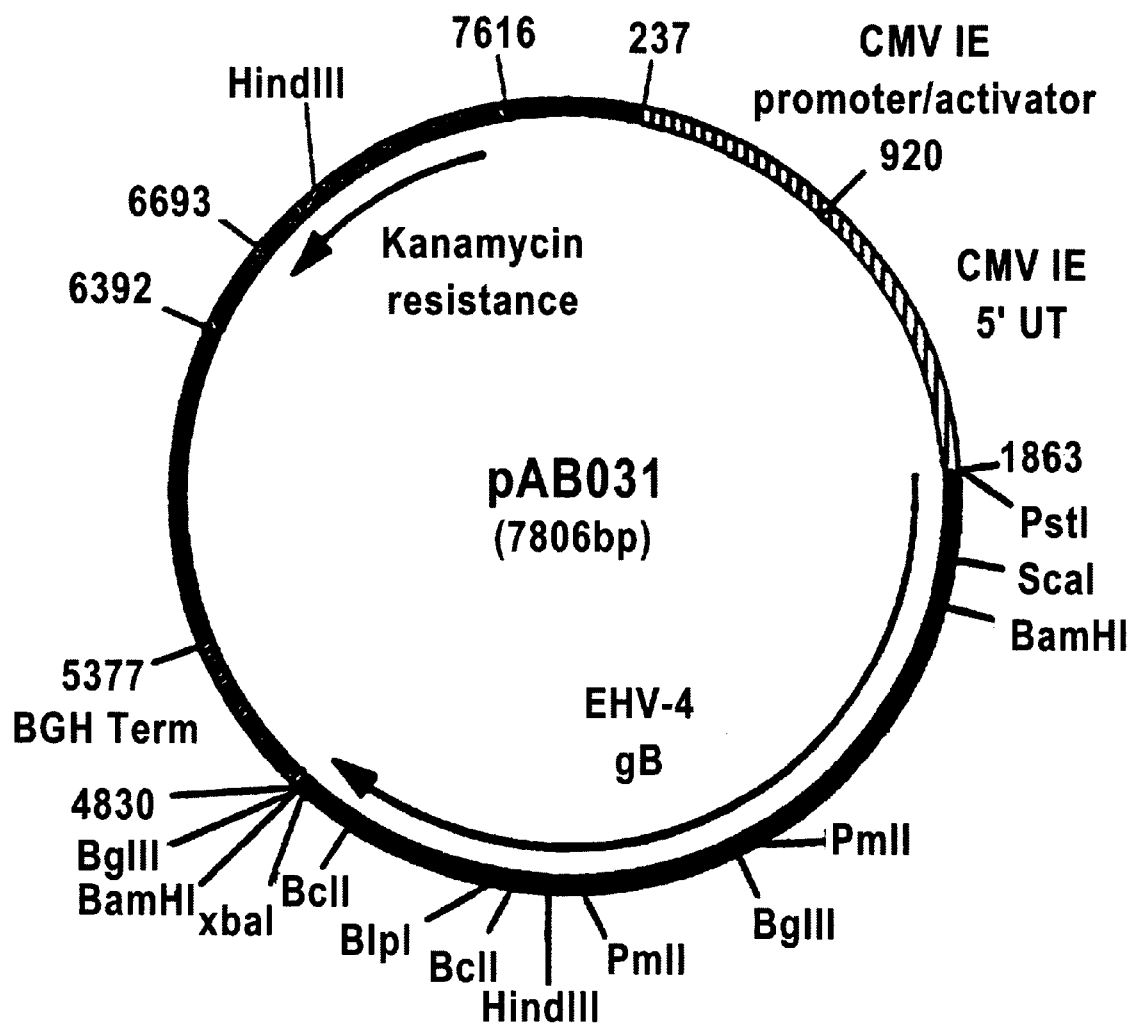
FIG. 3: Plasmid pAB031

This fragment was ligated to the vector pVR1012 (Example 7), which had previously been digested with PstI and XbaI, in order to yield the plasmid pAB031 (7806 bp) (FIG. 3).

Example 10

Constructing the Plasmid pAB013 (EHV-1 gD Gene)

A PCR reaction was carried out using the genomic DNA of type I equine herpesvirus (EHV-1) (Kentucky D strain) (J. C. Audonnet et al. J. Gen. Virol. 1990. 71. 2969–2978) and using the following oligonucleotides:

AB030 (32 mer) (SEQ ID No. 5)

5'AAAACTGCAGCATGTCTACCTTCAAGCTTATG 3'

AB031 (37 mer) (SEQ ID No. 6)

Figure 4:
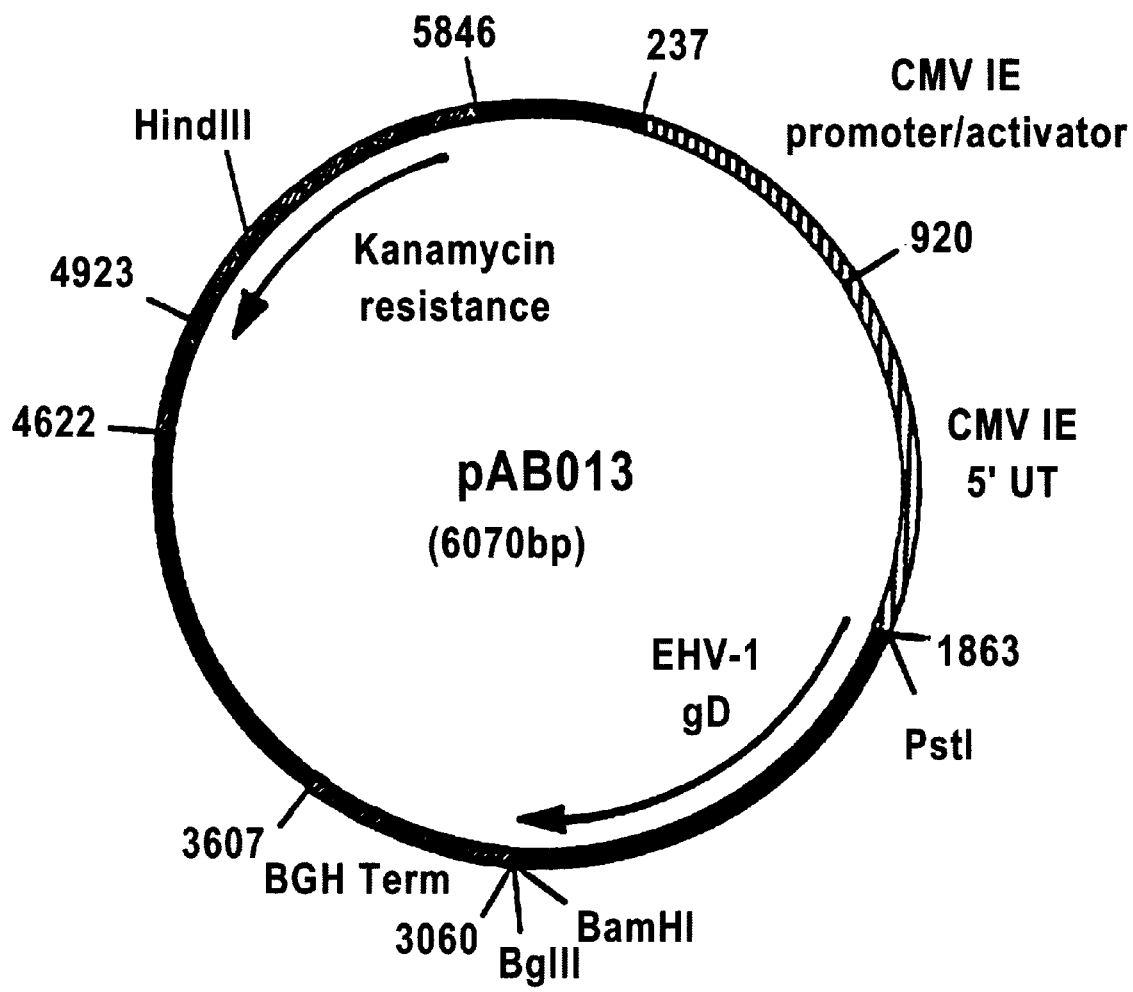
FIG. 4: Plasmid pAB013

5'CGCGGATCCTTACGGAAGCTGGG-TATATTTAACATCC 3' in order to isolate the gene encoding the gD glycoprotein (EHV-1 gD) in the form of a PstI/BamHI fragment. After purification, the 1228 bp PCR product was digested with pstI and BamHI in order to isolate a PstI/BamHI fragment of 1211 bp in size. This fragment was ligated to the vector pVR1012 (Example 7), which had previously been digested with PstI and BamHI, in order to yield the plasmid pAB013 (6070 bp) (FIG. 4).

Example 11

Constructing the Plasmid pAB032 (EHV-4 gD Gene)

A PCR reaction was carried out using the genomic DNA of type 4 equine herpesvirus (EHV-4) (A. Cullinane et al. J. Gen. Virol. 1993. 74. 1959–1964) and using the following oligonucleotides:

AB075 (33 mer) (SEQ ID No. 7)

5'AAAACTGCAGATATGTCTACCTTCAAGCCTATG 3'

AB076 (33 mer) (SEQ ID No. 8)

Figure 5:
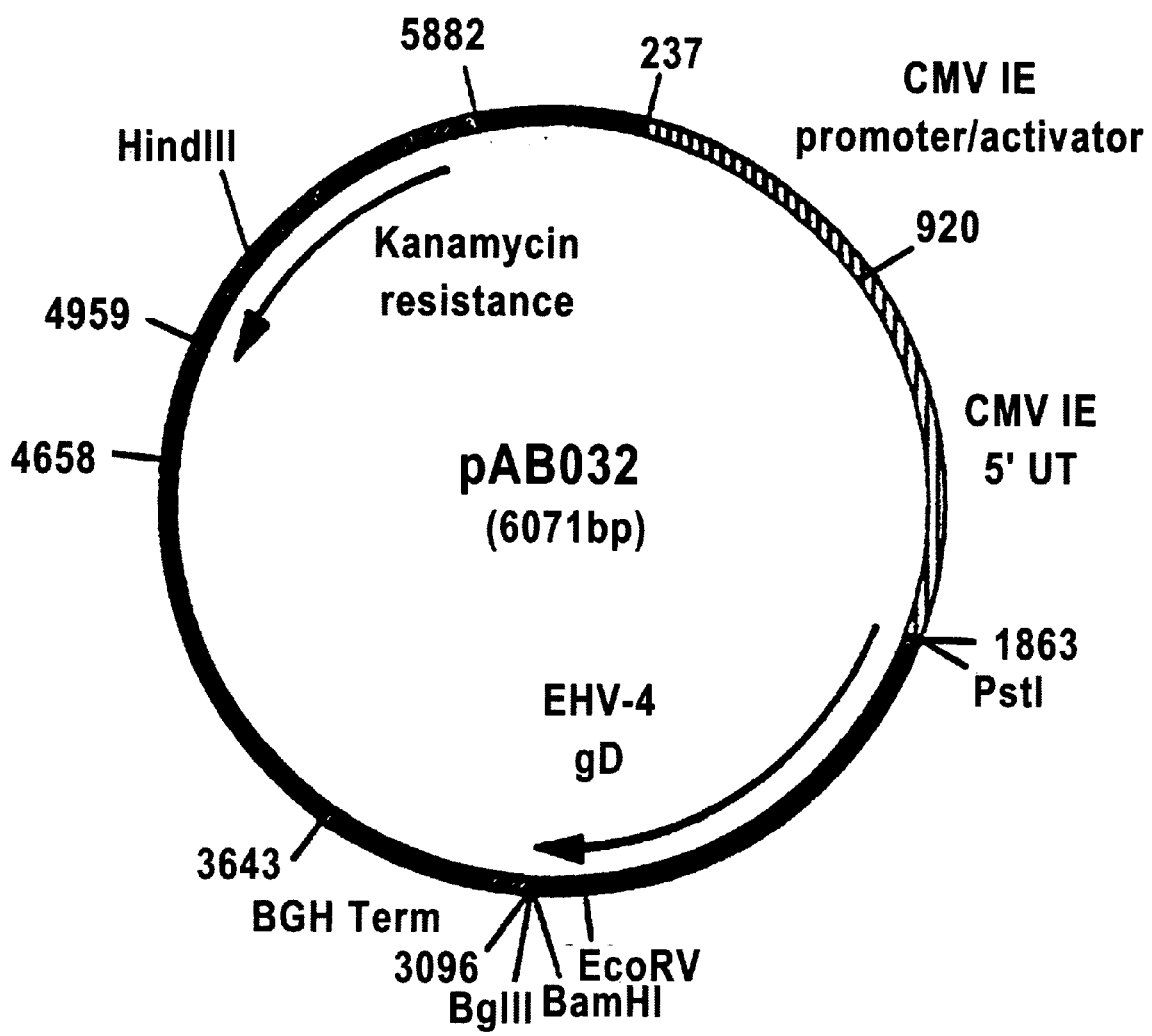
FIG. 5: Plasmid pAB032

5'CGCGGATCCTTACGGAAGCTGAGTATATTTGAC 3' in order to isolate the gene encoding the gD glycoprotein of EHV-4 (EHV-4 gD) in the form of a PstI/BamHI fragment. After purification, the 1230 bp PCR product was digested with PstI and BamHI in order to isolate a PstI/BamHI fragment of 1212 bp in size. This fragment was ligated to the vector pVR1012 (Example 7), which had previously been digested with PstI and BamHI, in order to yield the plasmid pAB032 (6071 bp) (FIG. 5).

Example 12

Constructing Plasmid pAB043 (HA Gene of the Prague Equine Influenza Strain)

An RT-PCR reaction was carried out, in accordance with the technique described in Example 6, using the genomic RNA of the equine influenza virus (EIV) (H7N7 Prague strain) (J. McCauley. Genbank sequence access No. =X62552), which was prepared in accordance with the technique described in Example 4, and using the following oligonucleotides:

AB015 (36 mer) (SEQ ID No. 9)

5'ACGCGTCGACATGAACACTCAAAT-TCTAATATTAGC 3'

AB016 (35 mer) (SEQ ID No. 10)

Figure 6:
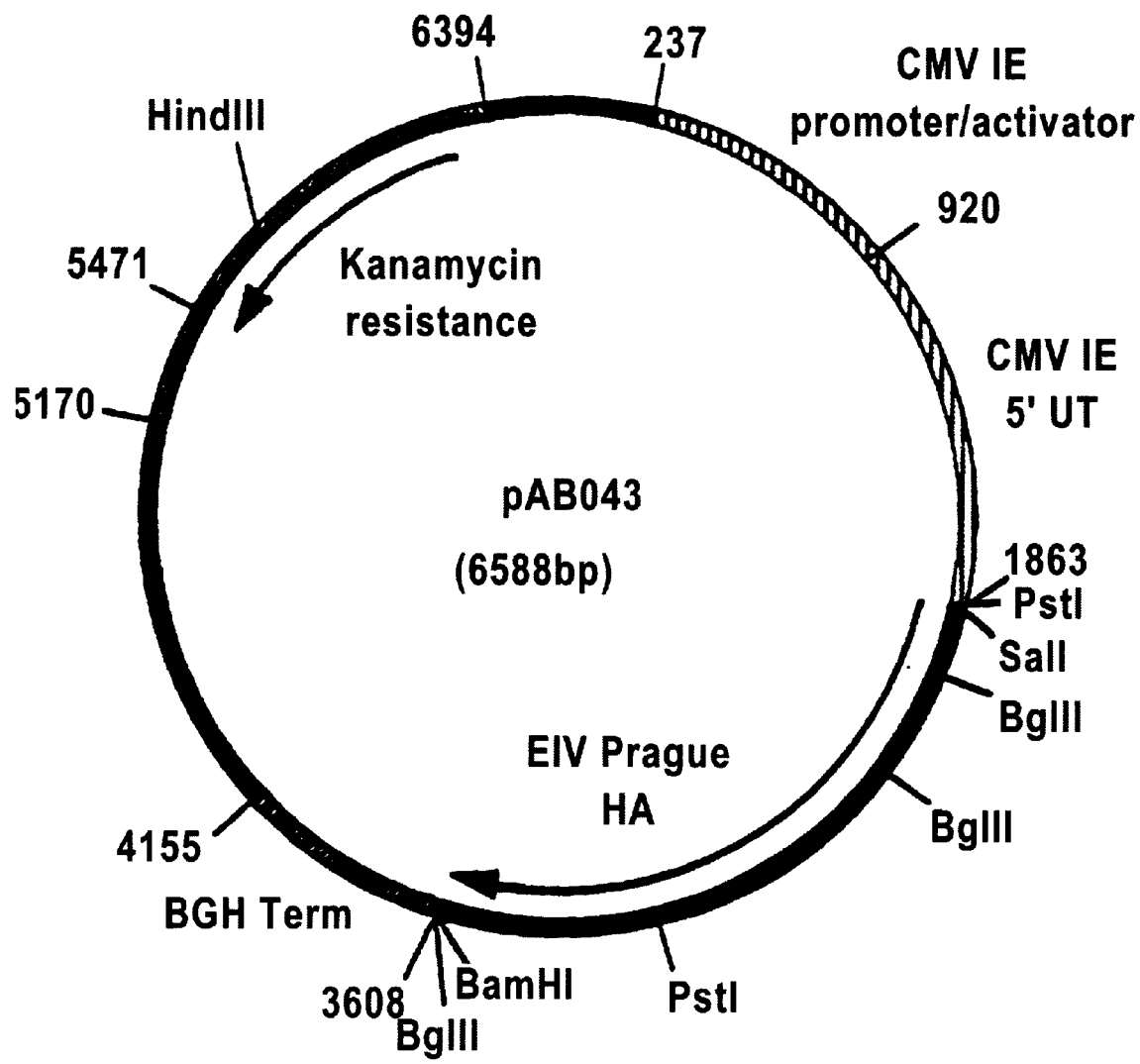
FIG. 6: Plasmid pAB043

5'CGCGGATCCCTTATATACAAATAGTG-CACCGCATG 3' in order to isolate the gene encoding the HA glycoprotein of the equine influenza virus in the form of a SalI/BamHI fragment. After purification, the 1733 bp RT-PCR product was digested with SalI and BamHI in order to isolate a SalI/BamHI fragment of 1720 bp in size. This fragment was ligated to the vector pVR1012 (Example 7), which had previously been digested with SalI and BamHI, in order to yield the plasmid pAB043 (6588 bp) (FIG. 6).

Example 13

Constructing the Plasmid pAB033 (HA Gene of the Suffolk Equine Influenza Strain)

An RT-PCR reaction was carried out, in accordance with the technique of Example 6, using the genomic RNA of the equine influenza virus (EIV) (Suffolk strain) (M. Binns. Genbank sequence access No. =X68437), which was prepared in accordance with the technique of Example 4, and using the following oligonucleotides:

AB077 (33 mer) (SEQ ID No. 11)

5'ACGCGTCGACGCATGAAGACAACCATTATTTTG 3'

AB078 (34 mer) (SEQ ID No. 12)

Figure 7:
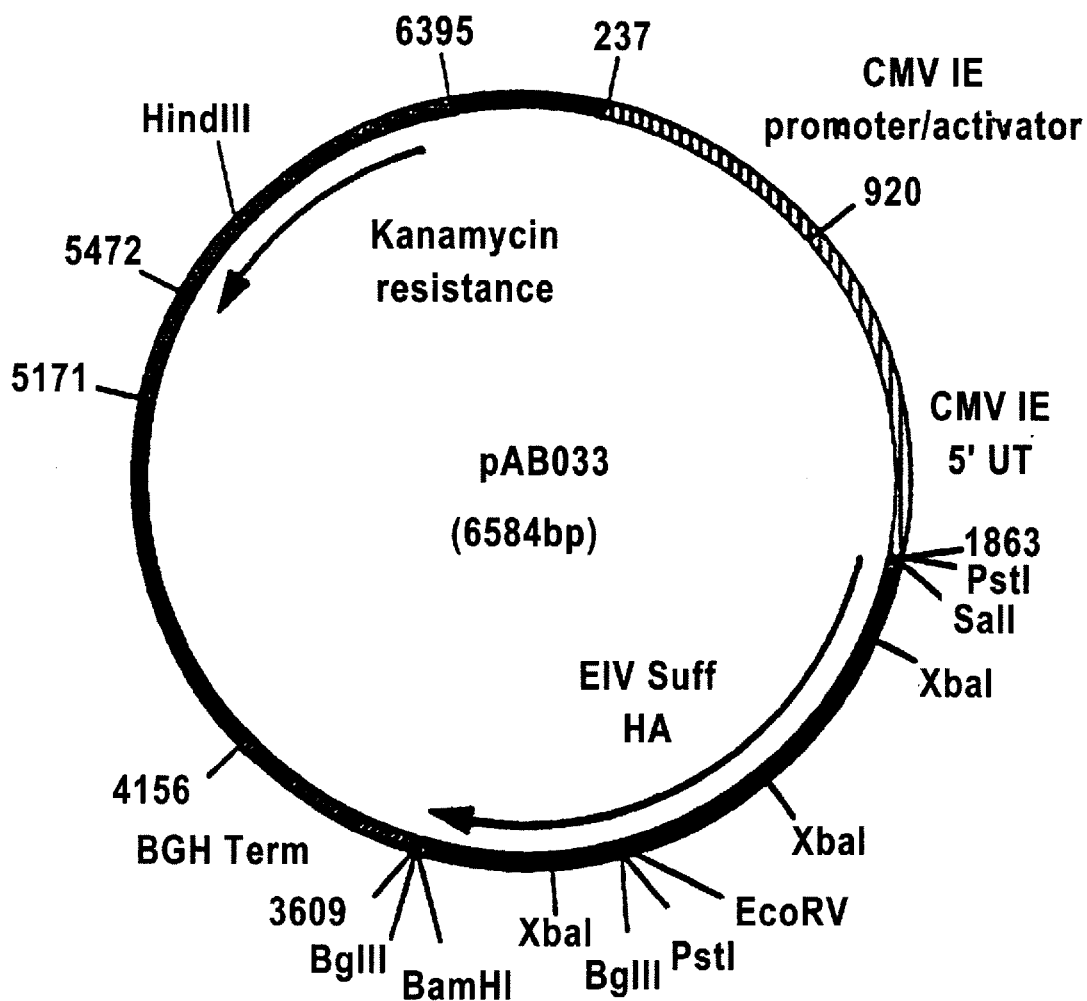
FIG. 7: Plasmid pAB033

5'CGCGGATCCTCAAATGCAAATGTTGCATCTGATG 3' in order to isolate the gene encoding the HA glycoprotein of the equine influenza virus in the form of a SalI/BamHI fragment. After purification, the 1729 bp RT-PCR product was digested with SalI and BamHI in order to isolate a SalI/BamHI fragment of 1717 bp in size. This fragment was ligated to the vector pVR1012 (Example 7), which had been previously digested with SalI and BamHI, in order to yield the plasmid pAB033 (6584 bp) (FIG. 7).

Example 14

Constructing the Plasmid pAB099 (HA Gene of the Fontainebleau Equine Influenza Strain)

An RT-PCR reaction was carried out, in accordance with Example 6, using the genomic RNA of the equine influenza virus (EIV) (Fontainebleau strain), which had been prepared in accordance with Example 4, and using the following oligonucleotides:

AB186 (32 mer) (SEQ ID No. 13)

5'TTTGCGGCCGCATCAAGACAACCATTATTTTG 3'

AB187 (35 mer) SQ ID No. 14)

Figure 9:
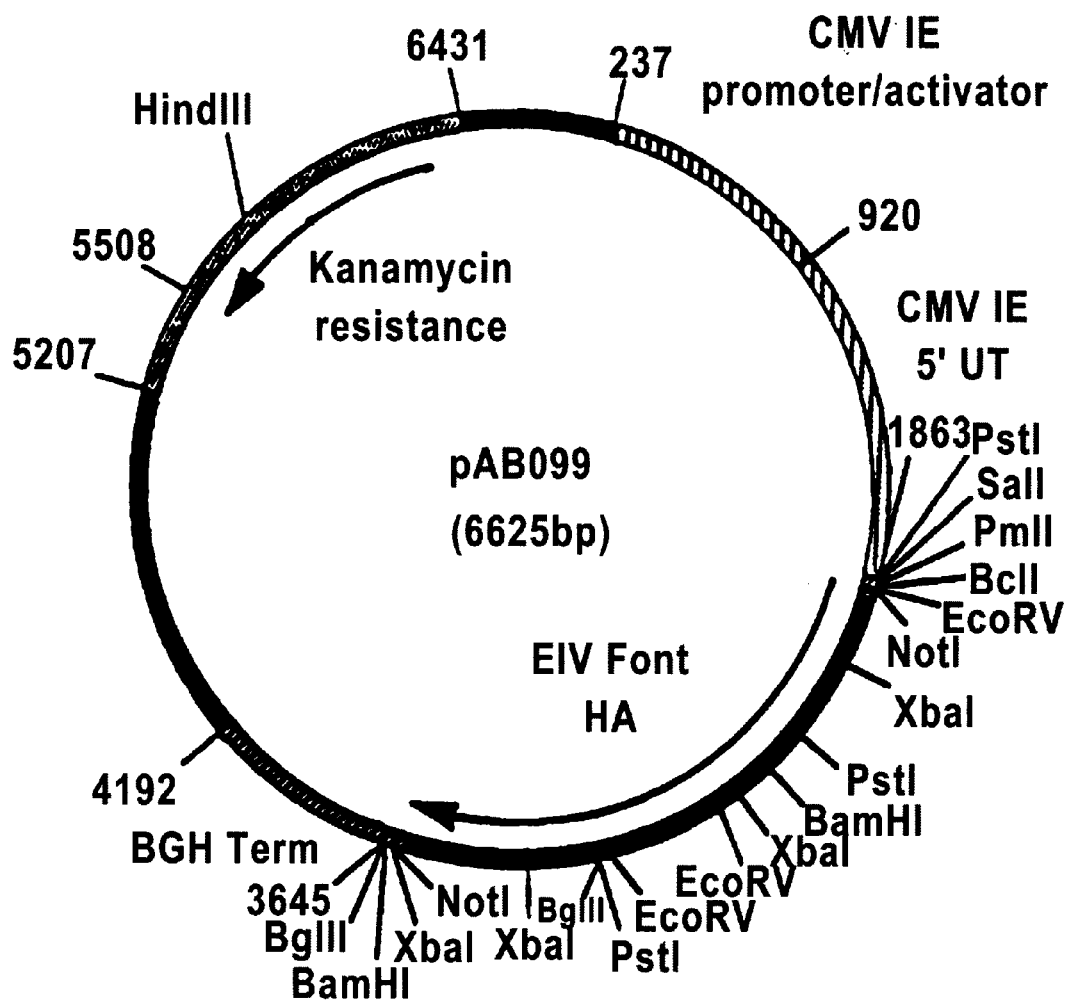
FIG. 9: Plasmid pAB099

5'TTTGCGGCCGCTTACTCAAATGCAAATGTTGCATC 3' in order to isolate the gene encoding the HA glycoprotein of the equine influenza virus (Fontainebleau strain) (FIG. 8 and SEQ ID No. 15) in the form of a NotI/NotI fragment. After purification, the 1724 bp RT-PCR product was digested with NotI in order to isolate a NotI/NotI fragment of 1710 bp in size. This fragment was ligated to the vector pVR1012 (Example 7) which had been previously digested with NotI, in order to yield the plasmid pAB099 (6625 bp), which contains the HA gene (Fontainebleau equine influenza strain) in the correct orientation with respect to the promotor (FIG. 9).

Example 15

Constructing the Plasmid pAB085 (NP Gene of the Prague Equine Influenza Strain)

An RT-PCR reaction was carried out, in accordance with the technique of Example 6, using the genomic RNA of the equine influenza virus (EIV) (H7N7 Prague strain) (O. Gorman et al. J. Virol. 1991. 65. 3704–3714), which was prepared in accordance with the technique of Example 4, and using the following oligonucleyotides:

AB156 (32 mer) (SEQ ID No. 16)

5'CCGGTCGACATGGCGTCTCAAGGCACCAAACG 3'

AB159 (34 mer) (SEQ ID No. 17)

Figure 10:
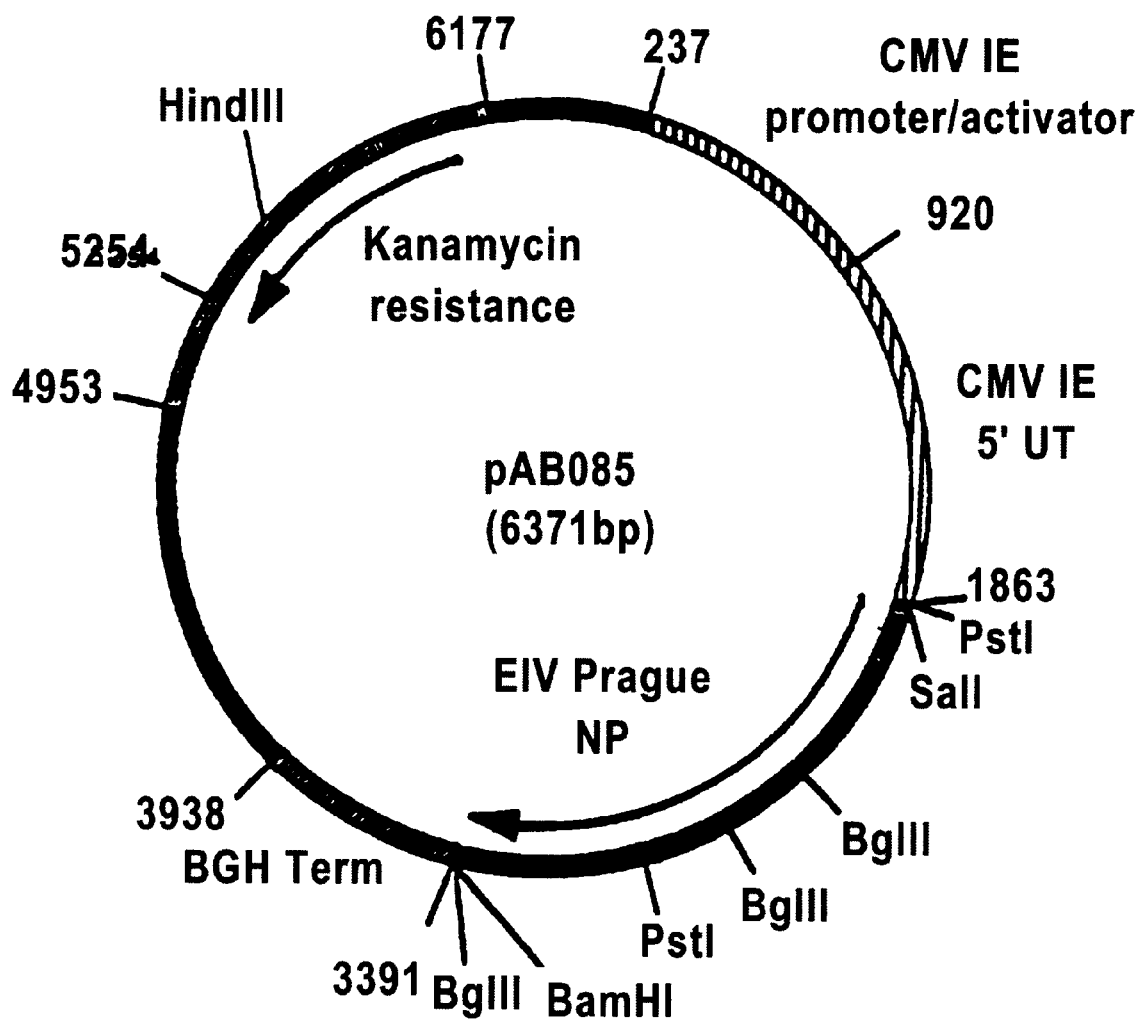
FIG. 10: Plasmid pAB085

5'CGCGGATCCTTAATTGTCAAACTCTTCTGCATTG 3' in order to isolate the gene encoding the NP nucleoprotein of the equine influenza virus in the form of a SalI/BamHI fragment. After purification, the 1515 bp RT-PCR product was digested with SalI and BamHI in order to isolate a SalI/BamHI fragment of 1503 bp in size. This fragment was ligated to the vector pVR1012 (Example 7), which had been previously digested with SalI and BamHI, in order to yield the Plasmid pAB085 (6371 bp) (FIG. 10).

Example 16

Constructing the Plasmid pAB084 (NP Gene of the Jillin Equine Influenza Strain)

An RT-PCR reaction was carried out, in accordance with the technique of Example 6, using the genomic RNA of the equine influenza virus (EIV) (H3N8 Jillin strain) (O. Gorman et al. J. Virol. 1991. 65. 3704–3714), which was prepared in accordance with the technique of Example 4, and using the following oligonucleotides:

AB156 (32 mer) (SEQ ID No. 16)

5'CCGGTCGACATGGCGTCTCAAGGCACCAAACG 3'

AB157 (34 mer) (SEQ ID No. 18)

Figure 11:
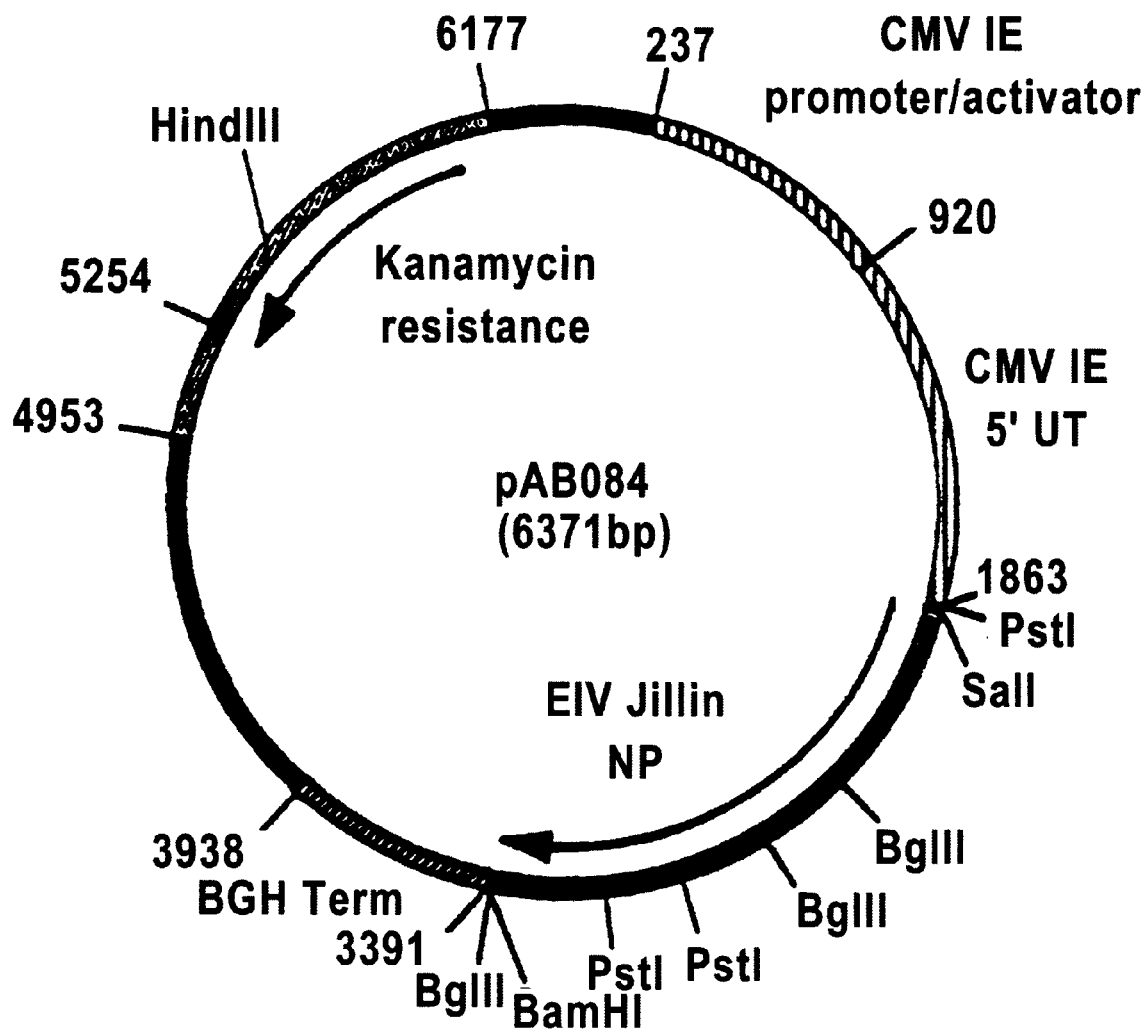
FIG. 11: Plasmid pAB084

5'CGCGGATCCTTAATTGTCATATTCCTCTGCATTG 3' in order to isolate the gene encoding the NP nucleoprotein of the equine influenza virus in the form of a SalI/BamHI fragment. After purification, the 1515 bp RT-PCR product was digested with SalI and SamHI in order to isolate a SalI/BamHI fragment of 1503 bp in size. This fragment was ligated to the vector pVR1012 (Example 7), which had been previously digested with SalI and BamHI, in order to yield the plasmid pAB084 (6371 bp) (FIG. 11).

Example 17

Constructing the Plasmid pAB070 (Tetanus Toxin C Subunit Gene)

An PCR reaction was carried out using the genomic DNA of *Clostridium tetani* (strain CN3911) (N. Fairweather et al. J. Bact. 1986. 165. 21–27), which was prepared in accordance with the technique of Example 2, and using the following oligonucleotides:

AB128 (34 mer) (SEQ ID No. 19)

5'AAACTGCAGATGAAAAATCTGGATTGTTGGGTTG 3'

AB129 (30 mer) (SEQ ID No. 20)

Figure 12:
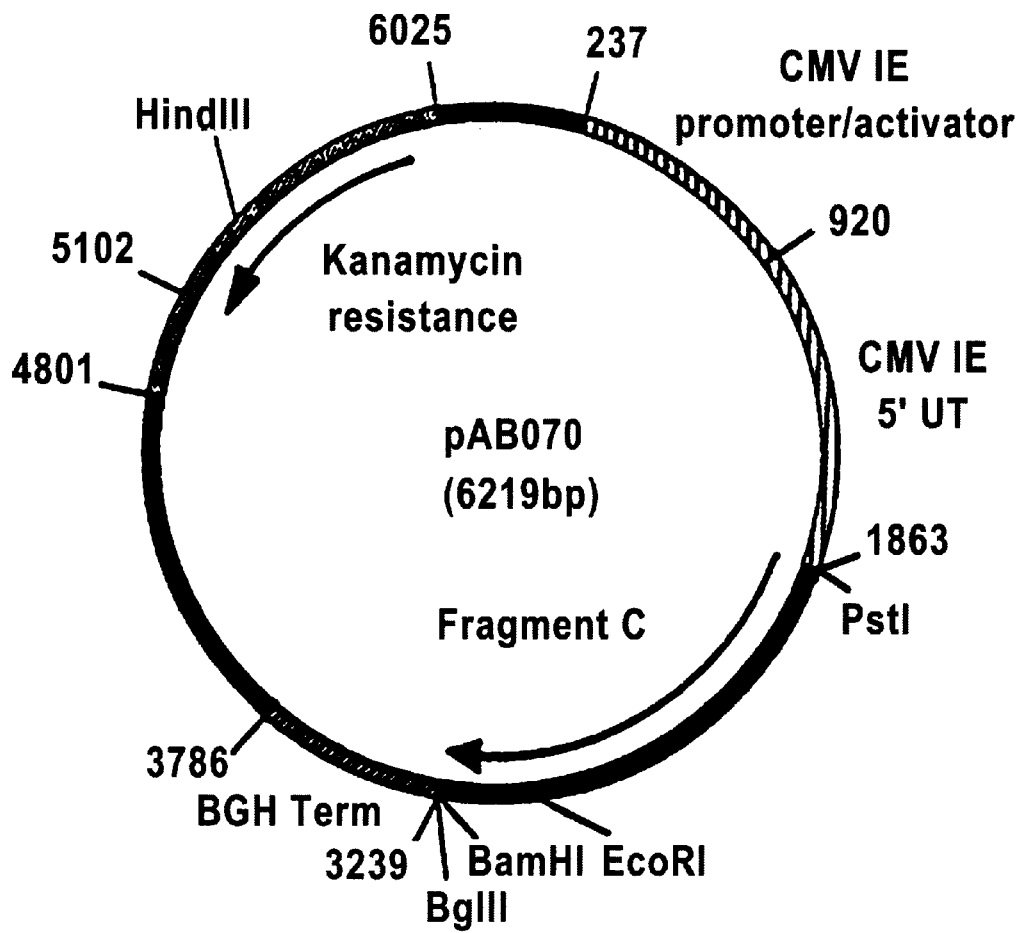
FIG. 12: Plasmid pAB070

5'TTTGGATCCTTAATCATTTGTCCATCCTTC 3' in order to isolate the sequence encoding the C subunit of the *Clostridium tetani* toxin in the form of a PstI/BamHI fragment. After purification, the 1377 bp PCR product was digested with PstI and BamHI in order to isolate a PstI/BamHI fragment of 1361 bp in size. This fragment was ligated to the vector pVR1012 (Example 7), which had been previously digested with PstI and BamHI, in order to yield the plasmid pAB070 (6219 bp) (FIG. 12).

Example 18

Constructing the Plasmid pAB017 (ospA Gene of *Borrelia burgdorferi*)

An PCR reaction was carried out using the genomic DNA of *Borrelia burgdorferi* (strain B31) (S. Bergstrom et al. Mol. Microbiol. 1989. 3. 479–486), which was prepared in accordance with the technique of Example 2, and using the following oligonucleotides:

AB038 (37 mer) (SEQ ID No. 21)

5'ACGCGTCGACTATGAAAAAATATTTAT-
TGGGAATAGG 3'

AB039 (34 mer) (SEQ ID No. 22)

Figure 13:
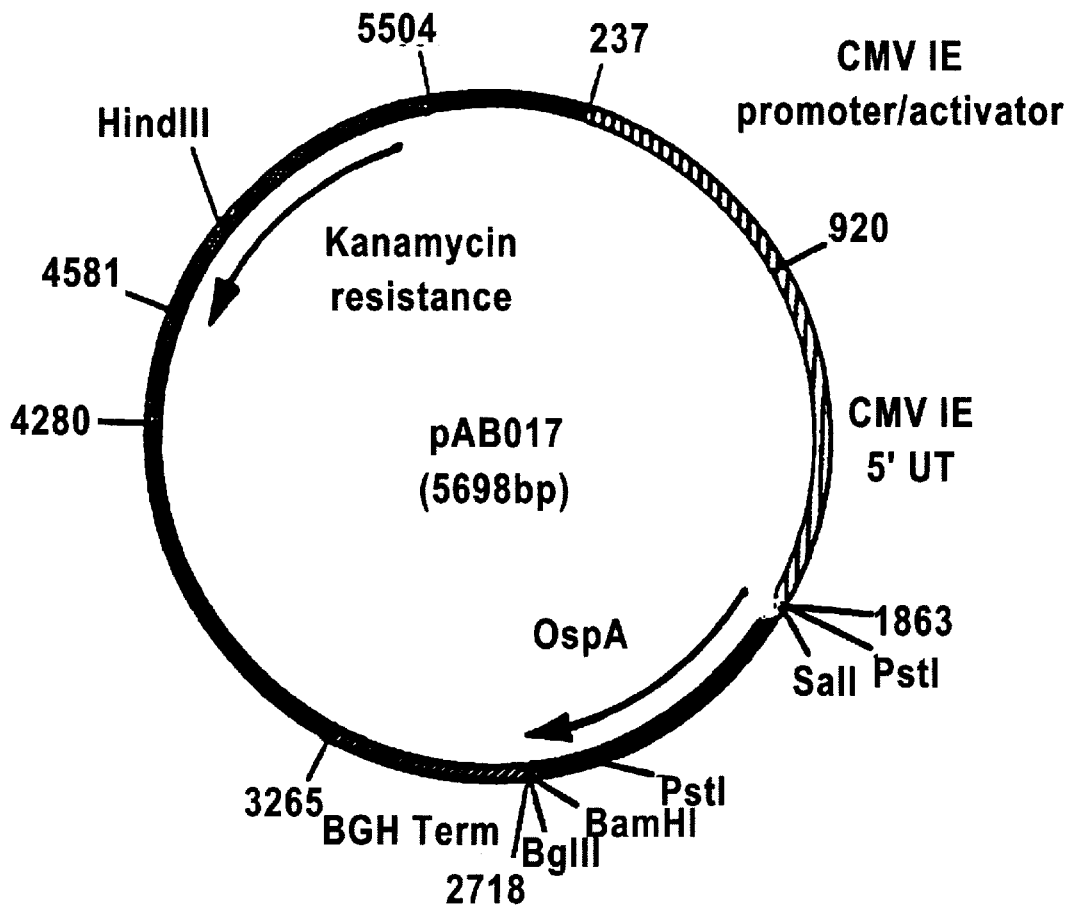
FIG. 13: Plasmid pAB017

5'CGCGGATCCCTTATTTTAAAGCGTTTTTAATTTC 3' in order to isolate the gene encoding the OspA membrane protein in the form of a SalI/BamHI fragment. After purification, the 842 bp PCR product was digested with SalI and BamHI in order to isolate a SalI/BamHI fragment of 829 bp in size. This fragment was ligated to the vector pVR1012 (Example 7), which had been previously digested with SalI and BamHI, in order to yield the plasmid pAB017 (5698 bp) (FIG. 13).

Example 19

Constructing the Plasmid pAB094 (E2 Gene of the Eastern Encephalomyelitis Virus)

An RT-PCR reaction was carried out, in accordance with the technique of Example 6, using the genomic RNA of the eastern encephalomyelitis virus (EEV) (North America 82V2137 strain) (S.Weaver et al. Virology. 1993. 197. 375–390), which was prepared in accordance with the technique of Example 4, and using the following oligonucleotides:

AB176 (34 mer) (SEQ ID No. 23)

5'AAACTGCAGATGGATTTGGACACT-
CATTTCACCC 3'

AB177 (44 mer) (SEQ ID No. 24)

Figure 14:
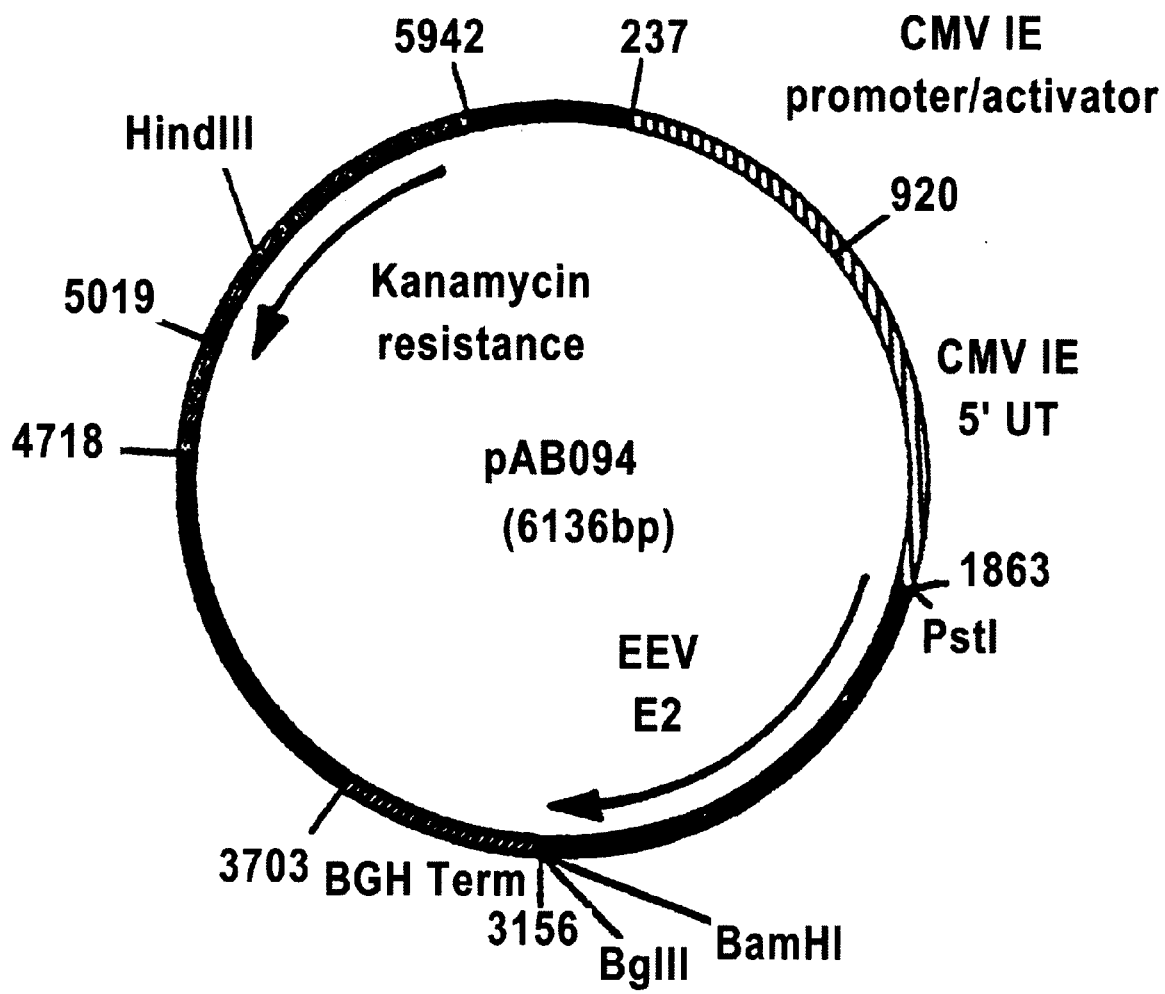
FIG. 14: Plasmid pAB094

5'CGCGGATCCTCAATAAAAATCATGC-
CCTCGTCGGCTTAATGCAG 3' in order to isolate the gene encoding the E2 glycoprotein of EEV in the form of a PstI/BamHI fragment. After purification, the 1294 bp RT-PCR product was digested with PstI and BamHI in order to isolate a PstI/BamHI fragment of 1278 bp in size. This fragment was ligated to the vector pVR1012 (Example 7) which had been previously digested with PstI and BamHI, in order to yield the plasmid pAB094 (6136 bp) (FIG. 14).

Example 20

Constructing the Plasmid pAB093 (C Gene of the Eastern Encephalomyelitis Virus)

An RT-PCR reaction was carried out, in accordance with the technique of Example 6, using the genomic RNA of the eastern encephalomyelitis virus (EEV) (North America 82V2137 strain) (S.Weaver et al. Virology. 1993. 197. 375–390), which was prepared in accordance with the technique of Example 4, and using the following oligonucleotides:

AB174 (33 mer) (SEQ ID No. 25)

5'AAACTGCAGATGTTCCCATACCCTACACTTAAC 3'

AB17S (45 mer) (SEQ ID No. 26)

Figure 15:
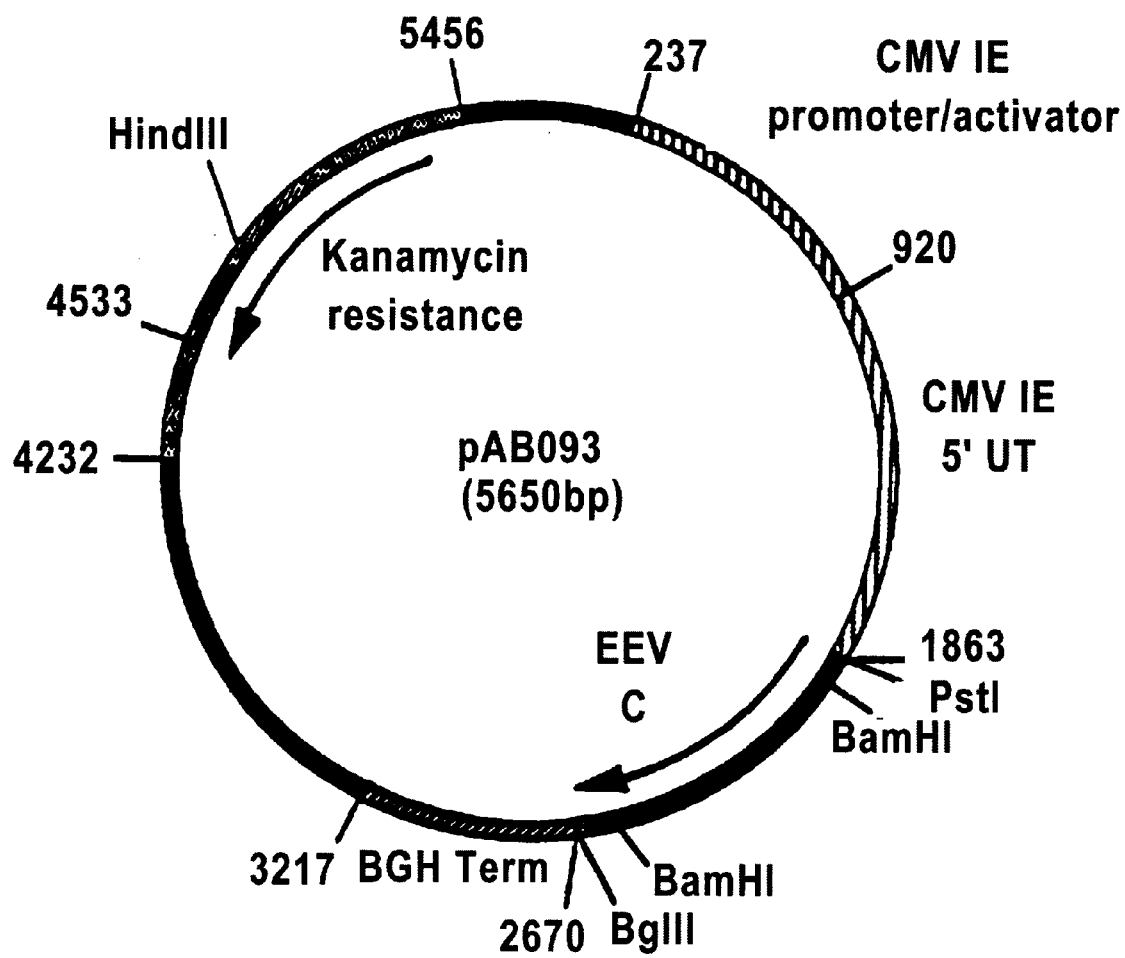
FIG. 15: Plasmid pAB093

5'TGAAGATCTTCAATAAAAATCACCATG-
GCTCTGACCCCTCTGGTG 3' in order to isolate the gene encoding the C capsid protein (EEV C) in the form of a PstI/BglII fragment. After purification, the 801 bp RT-PCR product was digested with PstI and BglII in order to isolate a PstI/BglII fragment of 785 bp in size. This fragment was ligated to the vector pVR1012 (Example 7), which had been previously digested with PstI and BglII, in order to yield the plasmid pAB093 (5650 bp) (FIG. 15).

Example 21

Constructing the Plasmid pAB096 (E2 Gene of the Western Encephalomyelitis Virus)

An RT-PCR reaction was carried out, in accordance with the technique of Example 6, using the genomic RNA of the western encephalomyelitis virus (WEV) (BSF 1703 strain) (C. Hahn et al. Proc. Natl. Acad. Sci. U.S.A. 1988. 85. 5997–6001), which was prepared in accordance with the technique of Example 4, and using the following oligonucleotides:

A3180 (35 mer) (SEQ ID No. 27)

5'ACGCGTCGACATGAGCATTACCGAT-
GACTTCACAC 3'

A3181 (44 mer) (SEQ ID No. 28)

Figure 16:
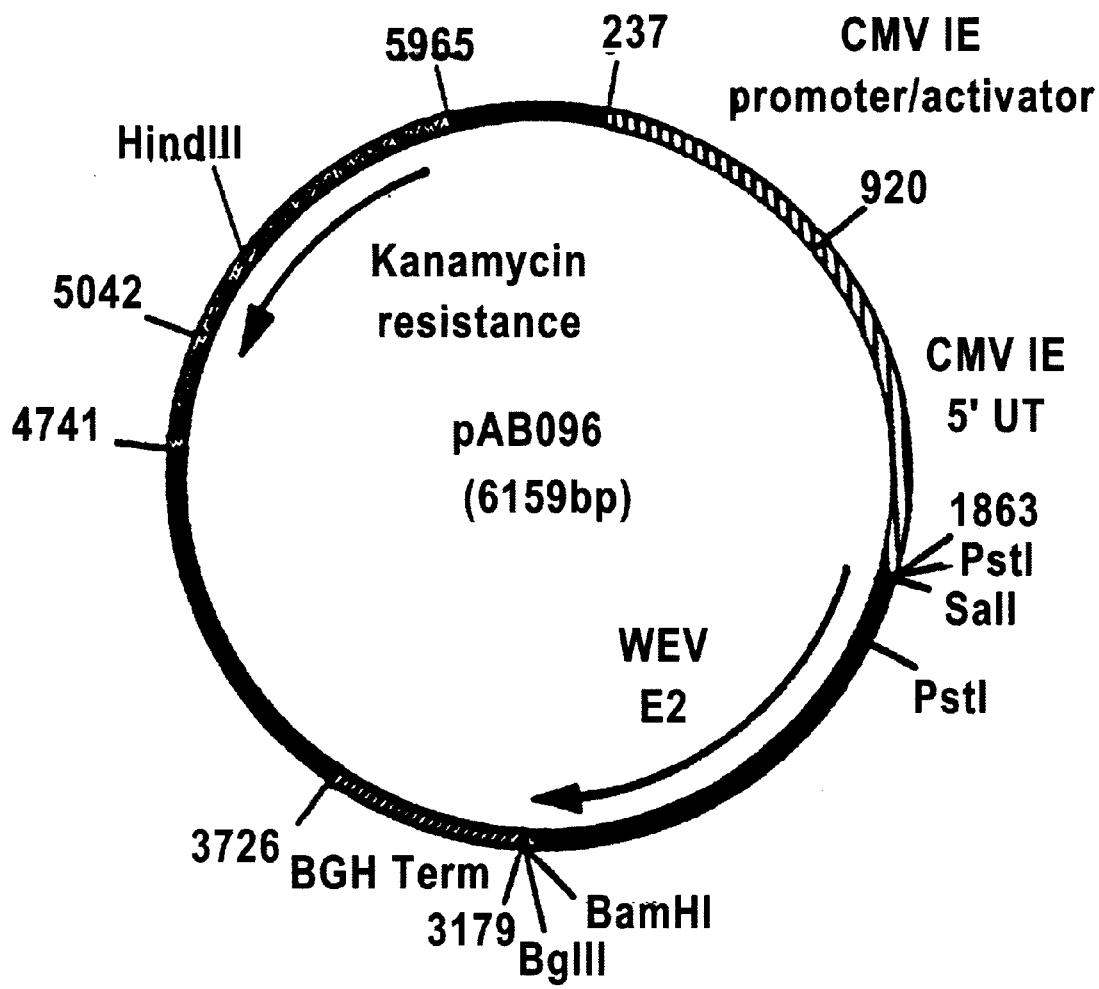
FIG. 16: Plasmid pAB096

5'CGCGGATCCTCAATAAAAATCAAGCGT-
TGGTTGGCCGAATACAG 3' in order to isolate the gene encoding the E2 glycoprotein of WEV in the form of a SalI/BamHI fragment. After purification, the 1304 bp RT-PCR product was digested with SalI and BamHI in order to isolate a SalI/BamHI fragment of 1291 bp in size. This fragment was ligated to the vector pVR1012 (Example 7), which had been previously digested with SalI and BamHI, in order to yield the plasmid pAB096 (6159 bp) (FIG. 16).

Example 22

Constructing the Plasmid pAB095 (C Gene of the Western Encephalomyelitis Virus)

An RT-PCR reaction was carried out, in accordance with Example 6, using the genomic RNA of the western encephalomyelitis virus (WEV) (BSF 1703 strain) (C. Hahn et al. Proc. Natl. Acad. Sci. U.S.A. 1988. 85. 5997–6001), which was prepared in accordance with Example 4, and using the following oligonucleotides:

AB178 (34 mer) (SEQ ID No. 29)

5'ACGCGTCGACATGTTTCCATACCCT-
CAGCTGAAC 3'

AB179 (44 mer) (SEQ ID No. 30)

Figure 17:
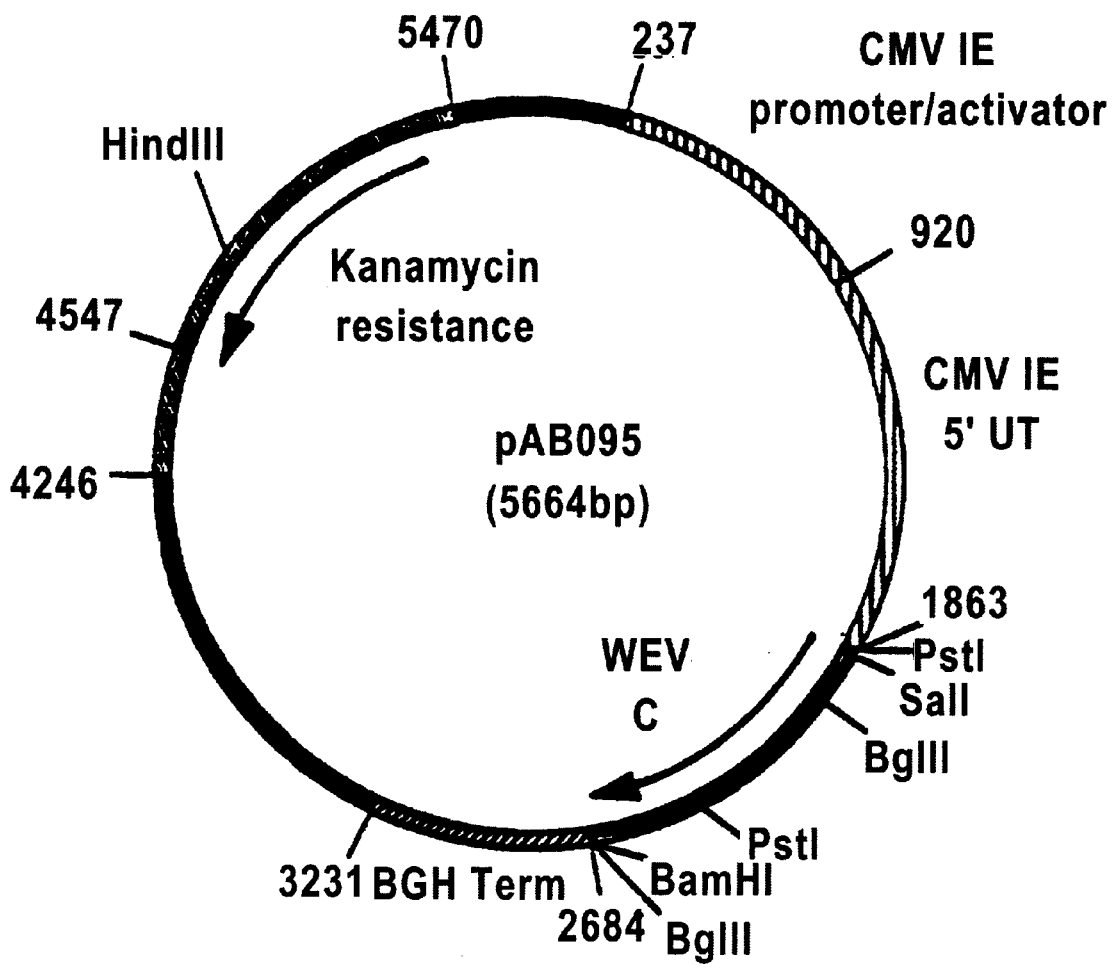
FIG. 17: Plasmid pAB095

5'CGCGGATCCTCAATAAAAATCACCACG-
GTTCAGAACCTTCGGGG 3' in order to isolate the gene encoding the C capsid protein of the WEV virus in the form of a SalI/BamHI fragment. After purification, the 809 bp RT-PCR product was digested with SalI and BamHI in order to isolate a SalI/BamHI fragment of 796 bp in size. This fragment was ligated to the vector pVR1012 (Example 7), which had been previously digested with SalI and BamHI, in order to yield the plasmid pAB09S (5664 bp) (FIG. 17).

Example 23

Constructing the Plasmid pAB098 (E2 Gene of the Venezuelan Encephalomyelitis Virus)

An RT-PCR reaction was carried out, in accordance with Example 6, using the genomic RNA of the Venezuelan encephalomyelitis virus (VEV) (P676 strain (type IC) (R. Kinney et al. Virology. 1992. 191. 569–580), which was prepared in accordance with Example 4, and using the following oligonucleotides:

AB184 (35 mer) (SEQ ID No. 31)

5'ACGCGTCGACATG.CCACCGAGGAGCT-
GTTAAGG 3'

AB185 (44 mer) (SEQ ID No. 32)

Figure 18:
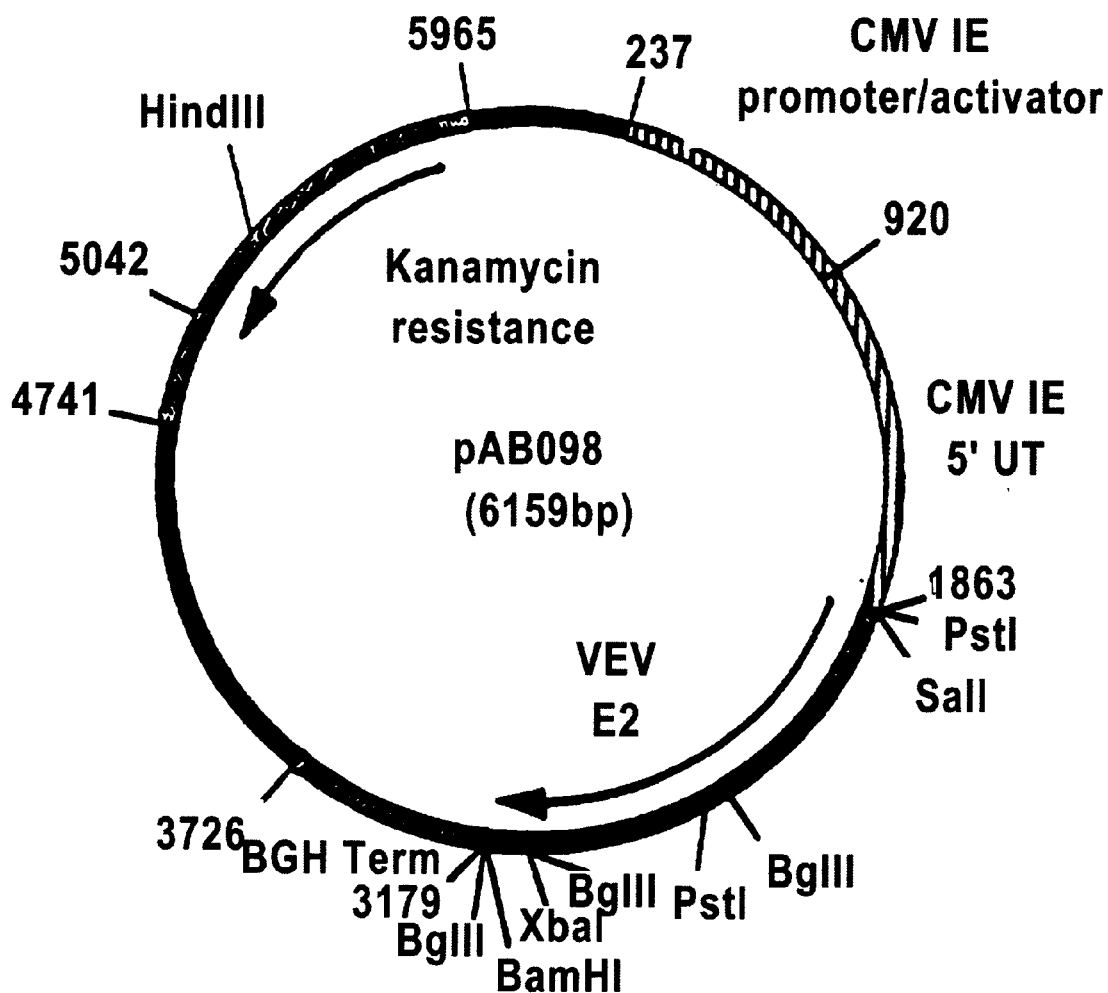
FIG. 18: Plasmid pAB098

5' C G C G G AT C C T C A ATA A A A AT C A G G C-CCGGGCAGTGCGGGCGCAG 3' in order to isolate the gene encoding the E2 glycoprotein of the VEV virus in the form of a SalI/BamHI fragment. After purification, the 1304 bp RT-PCR product was digested with SalI and BamHI in order to isolate a SalI/BamHI fragment of 1291 bp in size. This fragment was ligated to the vector pVR1012 (Example 7), which had been previously digested with SalI and BamHI, in order to yield the plasmid pAB098 (6159 bp) (FIG. 18).

Example 24

Constructing the Plasmid pAB097 (C Gene of the Venezuelan Encephalomyelitis Virus)

An RT-PCR reaction was carried out, in accordance with Example 6, using the genomic RNA of the Venezuelan encephalomyelitis virus (VEV) (P676 strain (type IC) (R. Kinney et al. Virology. 1992. 191. 569–580), which was prepared in accordance with Example 4, and using the following oligonucleotides:

AB182 (30 mer) (SEQ ID No. 33)

5'AAACTGCAGATGTTCCCGTTCCAGCCAATG 3'

AB183 (45 mer) (SEQ ID No. 34)

Figure 19:
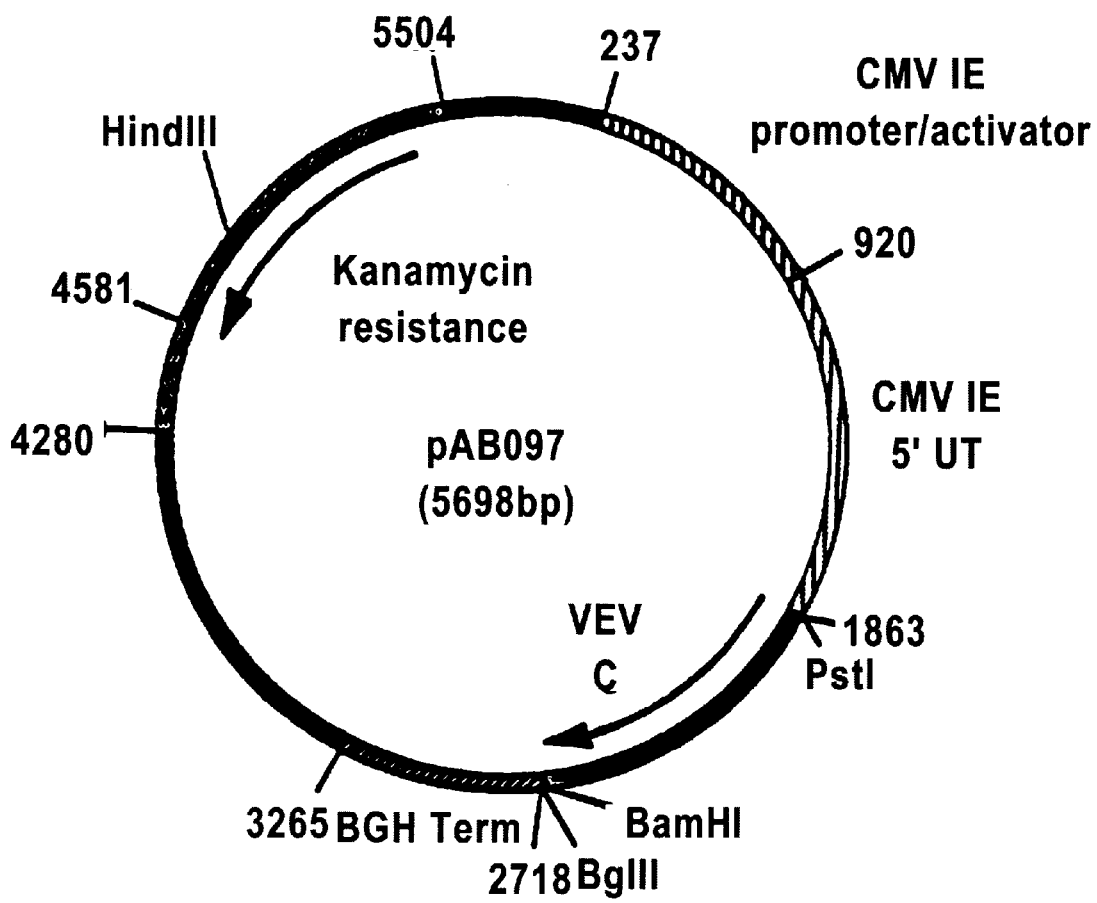
FIG. 19: Plasmid pAB097

5' C G C G G AT C C T C A ATA A A A AT C A C C AT-TGCTCGCAGTTCTCCGGAG 3' in order to isolate the gene encoding the C capsid protein of the VEV virus in the form of a PstI/SamHI fragment. After purification, the 856 bp RT-PCR product was digested with PstI and BamHI in order to isolate a PstI/BamHI fragment of 839 bp in size. This fragment was ligated to the vector pVR1012 (Example 7), which had been previously digested with PstI and BamHI, in order to yield the plasmid pAB097 (5698 bp) (FIG. 19).

Example 25

Constructing the Plasmid pAB041 (G Gene of the Rabies Virus)

An RT-PCR reaction was carried out, in accordance with Example 6, using the genomic RNA of the rabies virus (ERA strain) (A. Anilionis et al. Nature. 1981. 294. 275–278), which was prepared in accordance with Example 4, and using the following oligonucleotide:

AB011 (33 mer) (SEQ ID No. 35)

5' A A A A C T G C A G A G AT G G T T C C T C A G-GCTCTCCTG 3'

AB012 (34 mer) (SEQ ID No. 36)

Figure 20:
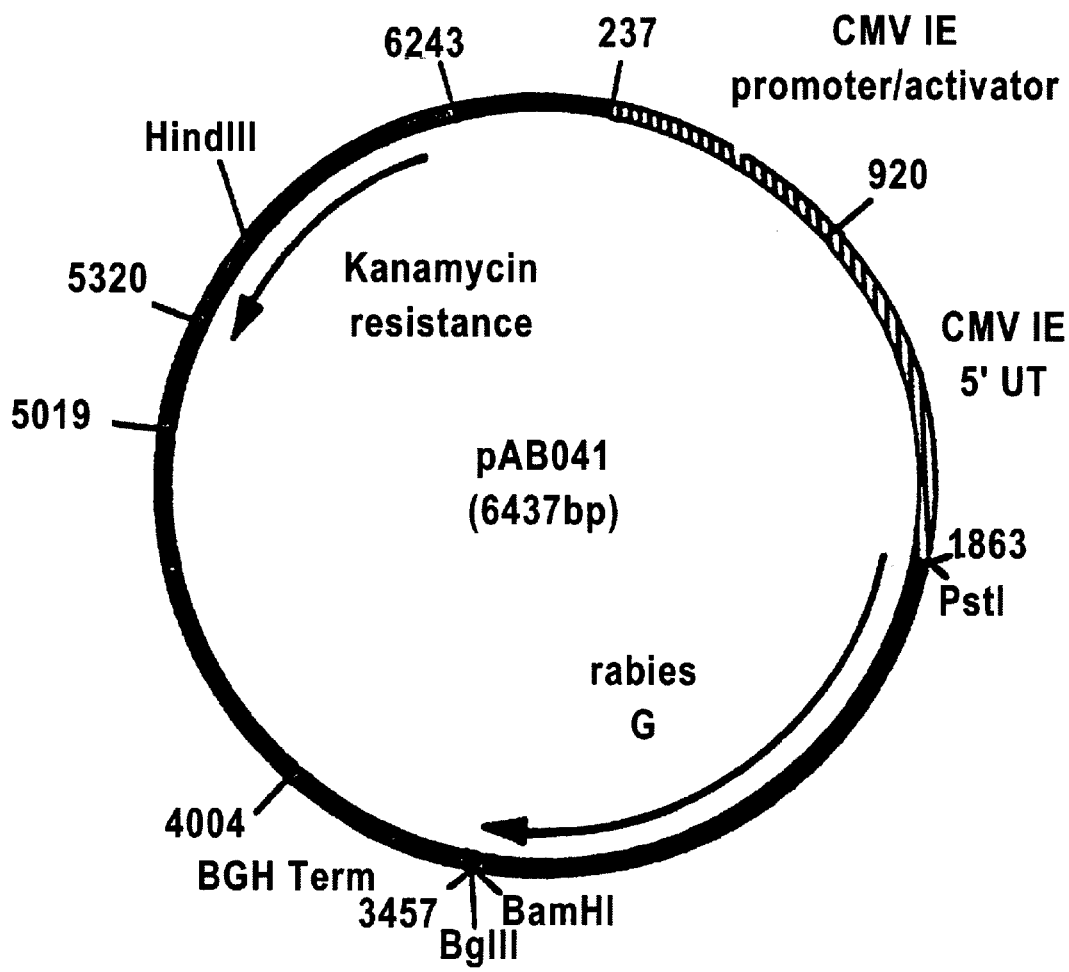
FIG. 20: Plasmid pAB041

5' C G C G G AT C C T C A C A G T C T G G T C T C A C-CCCCACTC 3' in order to amplify a 1589 bp fragment which contains the gene encoding the G protein of the rabies virus. After purification, the RT-PCR product was digested with PstI and BamHI in order to give a PstI/BamHI fragment of 1578 bp in size. This fragment was ligated to the vector pVR1012 (Example 7), which had been previously digested with PstI and BamHI, in order to yield the plasmid pAB041 (6437 bp) (FIG. 20).

Example 26

Preparing and Purifying Plasmids

In order to prepare plasmids intended for vaccinating animals, any technique can be used which makes it possible to obtain a suspension of purified plasmids which are in the main in supercoiled form. These techniques are well known to the skilled person. The technique which may in particular be mentioned is that of alkaline lysis followed by two consecutive ultra-centrifugations through a caesium chloride gradient in the presence of ethidium bromide, as described in J. Sambrook et al. (*Molecular Cloning: A Laboratory Manual.* 2nd Edition. Cold Spring Harbor Laboratory. Cold Spring Harbor. N.Y. 1989). The reader may also refer to patent applications PCT WO 95/21250 and PCT WO 96/02658, which describe industrial-scale methods for producing plasmids which can be used for vaccination. For the requirements of producing vaccines (see Example 17), the purified plasmids are resuspended so as to obtain solutions of high concentration (>2 mg/ml) which are compatible with being stored. In order to do this, the plasmids are resuspended either in ultrapure water or in TE buffer (10 mM tris-HCl; 1 mM EDTA, pH 8.0).

Example 27

Producing Combined Vaccines

The concentrated solutions (Example 16) of the various plasmids required for producing a combined vaccine are mixed. The mixtures are prepared in such a way that the final concentration of each plasmid corresponds to the effective dose of each plasmid. The solutions which can be used for adjusting the final concentration of the vaccine can be either an 0.9% NaCl solution or PBS buffer.

Special formulations, such as liposomes or cationic lipids, can also be used for producing the vaccines.

Example 28

Vaccinating Horses

The horses are vaccinated with doses of 100 $\mu$g, 250 $\mu$g or 500 $\mu$g per plasmid.

The injections can be carried out by the intramuscular route, using a needle, into the muscles of the neck. In this case, the vaccine doses are administered in a volume of 2 ml.

The injections can be carried out by the intradermal route using a liquid jet injection appliance (without needle) which delivers an 0.2 ml dose at 5 points (0.04 ml per injection point) (for example the "PIGJET" appliance). In this case, the vaccine doses are administered in volumes of 0.2 or 0.4 ml, corresponding, respectively, to one or two administrations. When two consecutive administrations are performed using the PIGJET appliance, these administrations are carried out with a spatial gap between them, such that the two injection areas are separated from each other by a distance of approximately 1 to 2 centimetres.

What is claimed is:

1. An immunogenic composition for inducing in an equine host an immunological response against equine rhinopneumonitis virus (EHV) comprising at least one plasmid that contains and expresses in vivo in an equine host cell nucleic acid molecule(s) having sequence(s) encoding EHV gB, gD, or gB and gD and a pharmaceutically acceptable carrier.

2. The immunogenic composition according to claim 1 which comprises a plasmid that contains and expresses in vivo in an equine host cell nucleic acid molecule(s) having sequences(s) encoding EHV gB and gD.

3. The immunogenic composition according to claim 1 which comprises a first plasmid that contains and expresses in vivo in an equine host cell a nucleic acid molecule having a sequence encoding EHV gB; and a second plasmid that contains and expresses in vivo in an equine host cell a nucleic acid molecule having a sequence encoding EHV gD.

4. The immunogenic composition according to claim 1 wherein the EHV is EHV-1.

5. The immunogenic composition according to claim 2 wherein the EHV is EHV-1.

6. The immunogenic composition according to claim 3 wherein the EHV is EHV-1.

7. The immunogenic composition according to claim 1 wherein the EHV is EHV-4.

8. The immunogenic composition according to claim 2 wherein the EHV is EHV-4.

9. The immunogenic composition according to claim 3 wherein the EHV is EHV-4.

10. The immunogenic composition according to claim 1 wherein the nucleic acid molecule(s) comprise a nucleic acid molecule from EHV-1 and a nucleic acid molecule from EHV-4.

11. The immunogenic composition according to claim 2 wherein the nucleic acid molecule(s) comprise a nucleic acid molecule from EHV-1 and a nucleic acid molecule from EHV-4.

12. The immunogenic composition according to claim 3 wherein the nucleic acid molecule(s) comprise a nucleic acid molecule from EHV-1 and a nucleic acid molecule from EHV-4.

13. An immunogenic composition for inducing in an equine host an immunological response against encephalomyelitis virus comprising at least one plasmid that contains and expresses in vivo in an equine host cell nucleic acid molecule(s) having sequence(s) encoding encephalomyelitis virus C, E2, or C and E2 proteins and a pharmaceutically acceptable carrier.

14. The immunogenic composition according to claim 13 which comprises a plasmid that contains and expresses in vivo in an equine host cell a nucleic acid molecule having a sequence encoding encephalomyelitis virus E2 protein.

15. The immunogenic composition according to claim 13 which comprises a first plasmid that contains and expresses in vivo in an equine host cell a nucleic acid molecule having a sequence encoding encephalomyelitis virus C protein; and a second plasmid that contains and expresses in vivo in an equine host cell a nucleic acid molecule having a sequence encoding encephalomyelitis virus E2 proteins.

16. The immunogenic composition according to claim 13 which comprises a plasmid that contains and expresses in vivo in an equine host cell nucleic acid molecule(s) having sequence(s) encoding encephalomyelitis virus C and E2 proteins.

17. The immunogenic composition according to claim 13 wherein the encephalomyelitis virus is selected from the group consisting of Eastern encephalomyelitis virus, Western encephalomyclitis virus and Venezuelan encephalomyelitis virus.

18. The immunogenic composition according to claims 14 wherein the encephalomyelitis virus is selected from the group consisting of Eastern encephalomyelitis virus, Western encephalomyelitis virus and Venezuelan encephalomyelitis virus.

19. The immunogenic composition according to claim 15 wherein the encephalomyelitis virus is selected from the group consisting of Eastern encephalomyelitis virus, Western encephalomyelitis virus and Venezuelan encephalomyelitis virus.

20. The immunogenic composition according to claim 16 wherein the encephalomyelitis virus is selected from the group consisting of Eastern encephalomyelitis virus, Western encephalomyelitis virus and Venezuelan encephalomyelitis virus.

21. The immunogenic according to claim 13 wherein the nucleic acid molecule(s) comprise a nucleic acid molecule from Eastern encephalomyelitis virus, a nucleic acid molecule from Western encephalomyelitis virus, and a nucleic acid molecule from Venezuelan encephalomyelitis virus.

22. The immunogenic according to claim 14 wherein the nucleic acid molecule(s) comprise a nucleic acid molecule from Eastern encephalomyelitis virus, a nucleic acid molecule from Western encephalomyelitis virus, and a nucleic acid molecule from Venezuelan encephalomyelitis virus.

23. The immunogenic according to claim 15 wherein the nucleic acid molecule(s) comprise a nucleic acid molecule from Eastern encephalomyelitis virus, a nucleic acid molecule from Western encephalomyelitis virus, and a nucleic acid molecule from Venezuelan encephalomyelitis virus.

24. The immunogenic according to claim 16 wherein the nucleic acid molecule(s) comprise a nucleic acid molecule from Eastern encephalomyelitis virus, a nucleic acid molecule from Western encephalomyelitis virus, and a nucleic acid molecule from Venezuelan encephalomyelitis virus.

25. A method for inducing an immunological response in an equine comprising: administering to said equine a vaccine selected from the group consisting of a live whole vaccine, an inactivated whole vaccine, a subunit vaccine, and a recombinant vaccine; and thereafter, administering to said equine an immunogenic composition as claimed in any one of claims 1–12, and 13–24.

26. A method for inducing an immunological response in an equine comprising administering to said equine an immunogenic composition as claimed in any one of claims 1–12 and 13–24.

27. A kit comprising (i) an immunogenic composition according to any one of claims 1–12 and 13–24, and (ii) an equine vaccine selected from the group consisting of a live whole vaccine, an inactivated whole vaccine, a subunit vaccine, and recombinant vaccine.

* * * * *

UNITED STATES PATENT AND TRADEMARK OFFICE
CERTIFICATE OF CORRECTION

PATENT NO. : 6,207,166 B1
DATED : March 27, 2001
INVENTOR(S) : Jean Christophe Audonnet et al.

It is certified that error appears in the above-identified patent and that said Letters Patent is hereby corrected as shown below:

Claim 13,
Line 5, (Column 28, line 27), change "enccephalomyelitis" to -- encephalomyelitis --.

Claim 17,
Line 4, (Column 28, line 48), change, "encephalomyclitis" to -- encephalomyelitis --.

Signed and Sealed this

Sixteenth Day of October, 2001

Attest:

NICHOLAS P. GODICI
Attesting Officer
Acting Director of the United States Patent and Trademark Office